US011116513B2

(12) United States Patent
Dinino et al.

(10) Patent No.: US 11,116,513 B2
(45) Date of Patent: Sep. 14, 2021

(54) MODULAR SURGICAL CLIP CARTRIDGE

(71) Applicant: Covidien LP, Mansfield, MA (US)

(72) Inventors: Matthew A. Dinino, Newington, CT (US); Brandon L. Calavan, Windsor, CT (US); Jacob C. Baril, Norwalk, CT (US); Roy J. Pilletere, North Haven, CT (US); Justin Thomas, New Haven, CT (US)

(73) Assignee: COVIDIEN LP, Mansfield, MA (US)

( * ) Notice: Subject to any disclaimer, the term of this patent is extended or adjusted under 35 U.S.C. 154(b) by 392 days.

(21) Appl. No.: 16/120,571

(22) Filed: Sep. 4, 2018

(65) Prior Publication Data

US 2019/0133594 A1 May 9, 2019

Related U.S. Application Data

(60) Provisional application No. 62/581,134, filed on Nov. 3, 2017.

(51) Int. Cl.
*A61B 17/122* (2006.01)
*A61B 17/00* (2006.01)

(52) U.S. Cl.
CPC ...... *A61B 17/1222* (2013.01); *A61B 2017/00477* (2013.01)

(58) Field of Classification Search
CPC ...... A61B 17/1222; A61B 2017/00477; B65D 21/0204

(Continued)

(56) References Cited

U.S. PATENT DOCUMENTS

| 3,120,230 A | 2/1964 | Skold |
| 3,363,628 A | 1/1968 | Wood |

(Continued)

FOREIGN PATENT DOCUMENTS

| AU | 2013254887 A1 | 11/2013 |
| CA | 1163889 A | 3/1984 |

(Continued)

OTHER PUBLICATIONS

International Search Report and Written Opinion corresponding to counterpart Int'l Appln. No. PCT/US2018/058078 dated Feb. 22, 2019.

(Continued)

*Primary Examiner* — J. Gregory Pickett
*Assistant Examiner* — Tia Cox

(57) ABSTRACT

A modular clip cartridge includes a body portion having a first wall and a second wall. The first wall defines a first protuberance, a second protuberance symmetrically opposed to the first protuberance, and a first mating feature disposed between the first and second protuberances. The second wall defines a first recess, a second recess symmetrically opposed to the first recess, and a second mating feature disposed between the first and second recesses. At least one clip compartment is defined in the body portion and configured to releasably retain at least one surgical clip therein. One of the first and second mating features of the modular clip cartridge is configured to selectively engage one of a first and a second mating feature of another modular clip cartridge to selectively connect the first modular clip cartridge and another modular clip cartridge into a unitary arrangement to define a modular surgical clip pack.

22 Claims, 3 Drawing Sheets

(58) Field of Classification Search
USPC .................................. 206/363, 339, 504
See application file for complete search history.

(56) References Cited

U.S. PATENT DOCUMENTS

| | | | |
|---|---|---|---|
| 3,638,847 A | 2/1972 | Noiles et al. | |
| 3,675,688 A | 7/1972 | Bryan et al. | |
| 3,735,762 A | 5/1973 | Bryan et al. | |
| 3,867,944 A | 2/1975 | Samuels | |
| 4,226,242 A | 10/1980 | Jarvik | |
| 4,242,902 A | 1/1981 | Green | |
| 4,296,751 A | 10/1981 | Blake, III et al. | |
| 4,328,902 A * | 5/1982 | North ................. | B65D 21/0204 |
| | | | 220/23.4 |
| 4,372,316 A | 2/1983 | Blake, III et al. | |
| 4,408,603 A | 10/1983 | Blake, III et al. | |
| 4,412,539 A | 11/1983 | Jarvik | |
| 4,418,694 A | 12/1983 | Beroff et al. | |
| 4,471,780 A | 9/1984 | Menges et al. | |
| 4,480,640 A | 11/1984 | Becht | |
| 4,480,641 A | 11/1984 | Failla et al. | |
| 4,484,403 A * | 11/1984 | Schwaller .......... | B65D 21/0204 |
| | | | 42/50 |
| 4,487,204 A | 12/1984 | Hrouda | |
| 4,487,205 A | 12/1984 | Di Giovanni et al. | |
| 4,491,133 A | 1/1985 | Menges et al. | |
| 4,492,232 A | 1/1985 | Green | |
| 4,498,476 A | 2/1985 | Cerwin et al. | |
| 4,500,024 A | 2/1985 | DiGiovanni et al. | |
| 4,509,518 A | 4/1985 | McGarry et al. | |
| 4,512,345 A | 4/1985 | Green | |
| 4,522,207 A | 6/1985 | Klieman et al. | |
| 4,532,925 A | 8/1985 | Blake, III | |
| 4,534,351 A | 8/1985 | Rothfuss et al. | |
| 4,545,377 A | 10/1985 | Cerwin et al. | |
| 4,549,544 A | 10/1985 | Favaron | |
| 4,556,058 A | 12/1985 | Green | |
| 4,557,263 A | 12/1985 | Green | |
| 4,562,839 A | 1/1986 | Blake, III et al. | |
| 4,572,183 A | 2/1986 | Juska | |
| 4,576,165 A | 3/1986 | Green et al. | |
| 4,576,166 A | 3/1986 | Montgomery et al. | |
| 4,590,937 A | 5/1986 | Deniega | |
| 4,598,711 A | 7/1986 | Deniega | |
| 4,602,631 A | 7/1986 | Funatsu | |
| 4,611,595 A | 9/1986 | Klieman et al. | |
| 4,612,932 A | 9/1986 | Caspar et al. | |
| 4,616,650 A | 10/1986 | Green et al. | |
| 4,616,651 A | 10/1986 | Golden | |
| 4,624,254 A | 11/1986 | McGarry et al. | |
| 4,637,395 A | 1/1987 | Caspar et al. | |
| 4,646,740 A | 3/1987 | Peters et al. | |
| 4,647,504 A | 3/1987 | Kimimura et al. | |
| 4,658,822 A | 4/1987 | Kees, Jr. | |
| 4,660,558 A | 4/1987 | Kees, Jr. | |
| 4,662,373 A | 5/1987 | Montgomery et al. | |
| 4,662,374 A | 5/1987 | Blake, III | |
| 4,671,278 A | 6/1987 | Chin | |
| 4,671,282 A | 6/1987 | Tretbar | |
| 4,674,504 A | 6/1987 | Klieman et al. | |
| 4,681,107 A | 7/1987 | Kees, Jr. | |
| 4,696,396 A | 9/1987 | Samuels | |
| 4,702,247 A | 10/1987 | Blake, III et al. | |
| 4,706,668 A | 11/1987 | Backer | |
| 4,712,549 A | 12/1987 | Peters et al. | |
| 4,726,372 A | 2/1988 | Perlin | |
| 4,733,666 A | 3/1988 | Mercer, Jr. | |
| 4,759,364 A | 7/1988 | Boebel | |
| 4,765,335 A | 8/1988 | Schmidt et al. | |
| 4,777,949 A | 10/1988 | Perlin | |
| 4,796,625 A | 1/1989 | Kees, Jr. | |
| 4,799,481 A | 1/1989 | Transue et al. | |
| 4,815,466 A | 3/1989 | Perlin | |
| 4,821,721 A | 4/1989 | Chin et al. | |
| 4,822,348 A | 4/1989 | Casey | |
| 4,834,096 A | 5/1989 | Oh et al. | |
| 4,850,355 A | 7/1989 | Brooks et al. | |
| 4,854,317 A | 8/1989 | Braun | |
| 4,856,517 A | 8/1989 | Collins et al. | |
| 4,929,239 A | 5/1990 | Braun | |
| 4,931,058 A | 6/1990 | Cooper | |
| 4,934,364 A | 6/1990 | Green | |
| 4,957,500 A | 9/1990 | Liang et al. | |
| 4,966,603 A | 10/1990 | Focelle et al. | |
| 4,967,949 A | 11/1990 | Sandhaus | |
| 4,983,176 A | 1/1991 | Cushman et al. | |
| 4,988,355 A | 1/1991 | Leveen et al. | |
| 5,002,552 A | 3/1991 | Casey | |
| 5,026,379 A | 6/1991 | Yoon | |
| 5,030,224 A | 7/1991 | Wright et al. | |
| 5,030,226 A | 7/1991 | Green et al. | |
| 5,032,127 A | 7/1991 | Frazee et al. | |
| 5,035,692 A | 7/1991 | Lyon et al. | |
| 5,047,038 A | 9/1991 | Peters et al. | |
| 5,049,152 A | 9/1991 | Simon et al. | |
| 5,049,153 A | 9/1991 | Nakao et al. | |
| 5,053,045 A | 10/1991 | Schmidt et al. | |
| 5,059,202 A | 10/1991 | Liang et al. | |
| 5,062,563 A | 11/1991 | Green et al. | |
| 5,062,846 A | 11/1991 | Oh et al. | |
| 5,078,731 A | 1/1992 | Hayhurst | |
| 5,084,057 A | 1/1992 | Green et al. | |
| 5,100,416 A | 3/1992 | Oh et al. | |
| 5,100,420 A | 3/1992 | Green et al. | |
| 5,104,394 A | 4/1992 | Knoepfler | |
| 5,104,395 A | 4/1992 | Thornton et al. | |
| 5,112,343 A | 5/1992 | Thornton | |
| 5,122,150 A | 6/1992 | Puig | |
| 5,127,915 A | 7/1992 | Mattson | |
| 5,129,885 A | 7/1992 | Green et al. | |
| 5,156,608 A | 10/1992 | Troidl et al. | |
| 5,160,339 A | 11/1992 | Chen et al. | |
| 5,163,945 A | 11/1992 | Ortiz et al. | |
| 5,171,247 A | 12/1992 | Hughett et al. | |
| 5,171,249 A | 12/1992 | Stefanchik et al. | |
| 5,171,250 A | 12/1992 | Yoon | |
| 5,171,251 A | 12/1992 | Bregen et al. | |
| 5,171,252 A | 12/1992 | Friedland | |
| 5,171,253 A | 12/1992 | Klieman | |
| 5,192,288 A | 3/1993 | Thompson et al. | |
| 5,197,970 A | 3/1993 | Green et al. | |
| 5,199,566 A | 4/1993 | Ortiz et al. | |
| 5,201,746 A | 4/1993 | Shichman | |
| 5,201,900 A | 4/1993 | Nardella | |
| 5,207,691 A | 5/1993 | Nardella | |
| 5,207,692 A | 5/1993 | Kraus et al. | |
| 5,217,473 A | 6/1993 | Yoon | |
| 5,219,353 A | 6/1993 | Garvey, III et al. | |
| 5,246,450 A | 9/1993 | Thornton et al. | |
| 5,269,792 A | 12/1993 | Kovac et al. | |
| 5,281,228 A | 1/1994 | Wolfson | |
| 5,282,807 A | 2/1994 | Knoepfler | |
| 5,282,808 A | 2/1994 | Kovac et al. | |
| 5,282,832 A | 2/1994 | Toso et al. | |
| 5,289,963 A | 3/1994 | McGarry et al. | |
| 5,290,299 A | 3/1994 | Fain et al. | |
| 5,300,081 A | 4/1994 | Young et al. | |
| 5,304,183 A | 4/1994 | Gourlay et al. | |
| 5,306,280 A | 4/1994 | Bregen et al. | |
| 5,306,283 A | 4/1994 | Conners | |
| 5,312,426 A | 5/1994 | Segawa et al. | |
| 5,316,159 A * | 5/1994 | Douglas ............. | B65D 21/0204 |
| | | | 206/432 |
| 5,330,442 A | 7/1994 | Green et al. | |
| 5,330,487 A | 7/1994 | Thornton et al. | |
| 5,340,360 A | 8/1994 | Stefanchik | |
| 5,342,373 A | 8/1994 | Stefanchik et al. | |
| 5,354,304 A | 10/1994 | Allen et al. | |
| 5,354,306 A | 10/1994 | Garvey, III et al. | |
| 5,356,064 A | 10/1994 | Green et al. | |
| 5,359,993 A | 11/1994 | Slater et al. | |
| 5,366,458 A | 11/1994 | Korthoff et al. | |
| 5,366,459 A | 11/1994 | Yoon | |
| 5,368,600 A | 11/1994 | Failla et al. | |

(56) References Cited

U.S. PATENT DOCUMENTS

| | | |
|---|---|---|
| 5,381,943 A | 1/1995 | Allen et al. |
| 5,382,253 A | 1/1995 | Hogendijk |
| 5,382,254 A | 1/1995 | McGarry et al. |
| 5,382,255 A | 1/1995 | Castro et al. |
| 5,383,880 A | 1/1995 | Hooven |
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,448,042 A | 9/1995 | Robinson et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,499 A | 1/1996 | Sorrentino et al. |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,562,655 A | 10/1996 | Mittelstadt et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,587 A | 5/1997 | Bishop et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,662 A | 9/1997 | Bishop et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,697,942 A | 12/1997 | Palti |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,743,310 A | 4/1998 | Moran |
| 5,749,881 A | 5/1998 | Sackier et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,827,323 A | 10/1998 | Klieman et al. |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,906,625 A | 5/1999 | Bito et al. |
| 5,913,862 A | 6/1999 | Ramsey et al. |
| 5,913,876 A | 6/1999 | Taylor et al. |
| 5,918,791 A | 7/1999 | Sorrentino et al. |
| 5,921,991 A | 7/1999 | Whitehead et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,009,551 A | 12/1999 | Sheynblat |
| 6,017,358 A | 1/2000 | Yoon et al. |
| 6,044,971 A * | 4/2000 | Esposito ............ A61B 17/1222 206/339 |
| 6,045,560 A | 4/2000 | McKean et al. |
| 6,053,908 A | 4/2000 | Crainich et al. |
| RE36,720 E | 5/2000 | Green et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |

(56) References Cited

U.S. PATENT DOCUMENTS

| | | | |
|---|---|---|---|
| 6,276,550 B1 * | 8/2001 | Cherrington | B65D 21/0204 |
| | | | 220/23.4 |
| 6,277,131 B1 | 8/2001 | Kalikow | |
| 6,306,149 B1 | 10/2001 | Meade | |
| 6,318,619 B1 | 11/2001 | Lee | |
| 6,322,571 B1 | 11/2001 | Adams | |
| 6,350,269 B1 | 2/2002 | Shipp et al. | |
| 6,352,541 B1 | 3/2002 | Kienzle et al. | |
| 6,391,035 B1 | 5/2002 | Appleby et al. | |
| 6,419,682 B1 * | 7/2002 | Appleby | A61B 17/1222 |
| | | | 206/339 |
| 6,423,079 B1 | 7/2002 | Blake, III | |
| 6,428,548 B2 | 8/2002 | Durgin et al. | |
| 6,440,144 B1 | 8/2002 | Bacher | |
| 6,461,363 B1 | 10/2002 | Gadberry et al. | |
| 6,464,710 B1 | 10/2002 | Foster | |
| 6,494,886 B1 | 12/2002 | Wilk et al. | |
| 6,517,536 B2 | 2/2003 | Hooven et al. | |
| 6,520,972 B2 | 2/2003 | Peters | |
| 6,527,786 B1 | 3/2003 | Davis et al. | |
| 6,537,289 B1 | 3/2003 | Kayan et al. | |
| 6,546,935 B2 | 4/2003 | Hooven | |
| 6,551,333 B2 | 4/2003 | Kuhns et al. | |
| 6,562,051 B1 | 5/2003 | Bolduc et al. | |
| 6,569,171 B2 | 5/2003 | DeGuillebon et al. | |
| 6,579,304 B1 | 6/2003 | Hart et al. | |
| 6,599,298 B1 | 7/2003 | Forster et al. | |
| 6,602,252 B2 | 8/2003 | Mollenauer | |
| 6,607,540 B1 | 8/2003 | Shipp | |
| 6,613,060 B2 | 9/2003 | Adams et al. | |
| 6,626,916 B1 | 9/2003 | Yeung et al. | |
| 6,626,922 B1 | 9/2003 | Hart et al. | |
| 6,648,898 B1 | 11/2003 | Baxter | |
| 6,652,538 B2 | 11/2003 | Kayan et al. | |
| 6,652,539 B2 | 11/2003 | Shipp et al. | |
| 6,656,193 B2 | 12/2003 | Grant et al. | |
| 6,673,083 B1 | 1/2004 | Kayan et al. | |
| 6,676,659 B2 | 1/2004 | Hutchins et al. | |
| 6,679,894 B2 | 1/2004 | Damarati | |
| RE38,445 E | 2/2004 | Pistl et al. | |
| 6,695,854 B1 | 2/2004 | Kayan et al. | |
| 6,706,057 B1 | 3/2004 | Bidoia et al. | |
| 6,716,226 B2 | 4/2004 | Sixto, Jr. et al. | |
| 6,723,109 B2 | 4/2004 | Solingen | |
| 6,733,514 B2 | 5/2004 | Miser | |
| 6,743,240 B2 | 6/2004 | Smith et al. | |
| 6,743,241 B2 | 6/2004 | Kerr | |
| 6,773,438 B1 | 8/2004 | Knodel et al. | |
| 6,773,440 B2 | 8/2004 | Gannoe et al. | |
| 6,776,783 B1 | 8/2004 | Frantzen et al. | |
| 6,776,784 B2 | 8/2004 | Ginn | |
| 6,780,195 B2 | 8/2004 | Porat | |
| 6,793,663 B2 | 9/2004 | Kneifel et al. | |
| 6,793,664 B2 | 9/2004 | Mazzocchi et al. | |
| 6,802,848 B2 | 10/2004 | Anderson et al. | |
| 6,814,742 B2 | 11/2004 | Kimura et al. | |
| 6,818,009 B2 | 11/2004 | Hart et al. | |
| 6,821,273 B2 | 11/2004 | Mollenauer | |
| 6,821,284 B2 | 11/2004 | Sturtz et al. | |
| 6,821,285 B2 | 11/2004 | Laufer et al. | |
| 6,824,547 B2 | 11/2004 | Wilson, Jr. et al. | |
| 6,824,548 B2 | 11/2004 | Smith et al. | |
| 6,835,199 B2 | 12/2004 | McGuckin, Jr. et al. | |
| 6,835,200 B2 | 12/2004 | Laufer et al. | |
| 6,837,893 B2 | 1/2005 | Miller | |
| 6,837,894 B2 | 1/2005 | Pugsley, Jr. et al. | |
| 6,837,895 B2 | 1/2005 | Mayenberger | |
| 6,840,945 B2 | 1/2005 | Manetakis et al. | |
| 6,843,794 B2 | 1/2005 | Sixto, Jr. et al. | |
| 6,849,078 B2 | 2/2005 | Durgin et al. | |
| 6,849,079 B1 | 2/2005 | Blake, III et al. | |
| 6,853,879 B2 | 2/2005 | Sunaoshi | |
| 6,869,435 B2 | 3/2005 | Blake, III | |
| 6,869,436 B2 | 3/2005 | Wendlandt | |
| 6,889,116 B2 | 5/2005 | Jinno | |
| 6,896,676 B2 | 5/2005 | Zubok et al. | |
| 6,896,682 B1 | 5/2005 | McClellan et al. | |
| 6,896,684 B2 | 5/2005 | Monassevitch et al. | |
| 6,905,503 B2 | 6/2005 | Gifford, III et al. | |
| 6,911,032 B2 | 6/2005 | Jugenheimer et al. | |
| 6,911,033 B2 | 6/2005 | de Guillebon et al. | |
| 6,913,607 B2 | 7/2005 | Ainsworth et al. | |
| 6,916,327 B2 | 7/2005 | Northrup, III et al. | |
| 6,916,332 B2 | 7/2005 | Adams | |
| 6,923,818 B2 | 8/2005 | Muramatsu et al. | |
| 6,939,356 B2 | 9/2005 | Debbas | |
| 6,942,674 B2 | 9/2005 | Belef et al. | |
| 6,942,676 B2 | 9/2005 | Buelna | |
| 6,945,978 B1 | 9/2005 | Hyde | |
| 6,945,979 B2 | 9/2005 | Kortenbach et al. | |
| 6,949,107 B2 | 9/2005 | McGuckin, Jr. et al. | |
| 6,953,465 B2 | 10/2005 | Dieck et al. | |
| 6,955,643 B2 | 10/2005 | Gellman et al. | |
| 6,959,852 B2 | 11/2005 | Shelton, IV et al. | |
| 6,960,218 B2 | 11/2005 | Rennich | |
| 6,960,221 B2 | 11/2005 | Ho et al. | |
| 6,962,594 B1 | 11/2005 | Thevenet | |
| 6,963,792 B1 | 11/2005 | Green | |
| 6,964,363 B2 | 11/2005 | Wales et al. | |
| 6,964,668 B2 | 11/2005 | Modesitt et al. | |
| 6,966,875 B1 | 11/2005 | Longobardi | |
| 6,966,917 B1 | 11/2005 | Suyker et al. | |
| 6,966,919 B2 | 11/2005 | Sixto, Jr. et al. | |
| 6,969,391 B1 | 11/2005 | Gazzani | |
| 6,972,023 B2 | 12/2005 | Whayne et al. | |
| 6,972,027 B2 | 12/2005 | Fallin et al. | |
| 6,973,770 B2 | 12/2005 | Schnipke et al. | |
| 6,974,462 B2 | 12/2005 | Sater | |
| 6,974,466 B2 | 12/2005 | Ahmed et al. | |
| 6,974,475 B1 | 12/2005 | Wall | |
| 6,981,505 B2 | 1/2006 | Krause et al. | |
| 6,981,628 B2 | 1/2006 | Wales | |
| 6,991,635 B2 | 1/2006 | Takamoto et al. | |
| 7,001,399 B2 | 2/2006 | Damarati | |
| 7,037,315 B2 | 5/2006 | Sancoff et al. | |
| 7,041,119 B2 | 5/2006 | Green | |
| 7,052,504 B2 | 5/2006 | Hughett | |
| 7,056,330 B2 | 6/2006 | Gayton | |
| 7,070,602 B2 | 7/2006 | Smith et al. | |
| 7,108,700 B2 | 9/2006 | Chan | |
| 7,108,703 B2 | 9/2006 | Danitz et al. | |
| 7,141,056 B2 | 11/2006 | Manetakis | |
| 7,144,402 B2 | 12/2006 | Kuester, III | |
| 7,175,648 B2 | 2/2007 | Nakao | |
| 7,179,265 B2 | 2/2007 | Manetakis et al. | |
| 7,207,997 B2 | 4/2007 | Shipp et al. | |
| 7,211,091 B2 | 5/2007 | Fowler et al. | |
| 7,211,092 B2 | 5/2007 | Hughett | |
| 7,213,736 B2 | 5/2007 | Wales et al. | |
| 7,214,230 B2 | 5/2007 | Brock et al. | |
| 7,214,232 B2 | 5/2007 | Bowman et al. | |
| 7,223,271 B2 | 5/2007 | Muramatsu et al. | |
| 7,223,272 B2 | 5/2007 | Francese et al. | |
| 7,232,445 B2 | 6/2007 | Kortenbach et al. | |
| 7,238,191 B2 | 7/2007 | Bachmann | |
| 7,261,724 B2 | 8/2007 | Molitor et al. | |
| 7,261,725 B2 | 8/2007 | Binmoeller | |
| 7,264,625 B1 | 9/2007 | Buncke | |
| 7,288,098 B2 | 10/2007 | Huitema et al. | |
| 7,297,149 B2 | 11/2007 | Vitali et al. | |
| 7,312,188 B2 | 12/2007 | Kiso | |
| 7,316,693 B2 | 1/2008 | Viola | |
| 7,316,696 B2 | 1/2008 | Wilson, Jr. et al. | |
| 7,322,995 B2 | 1/2008 | Buckman et al. | |
| 7,326,223 B2 | 2/2008 | Wilson, Jr. | |
| 7,329,266 B2 | 2/2008 | Royse et al. | |
| 7,331,968 B2 | 2/2008 | Arp et al. | |
| 7,338,503 B2 | 3/2008 | Rosenberg et al. | |
| 7,350,648 B2 * | 4/2008 | Gerstner | A47F 1/126 |
| | | | 206/509 |
| 7,357,805 B2 | 4/2008 | Masuda et al. | |
| 7,367,939 B2 | 5/2008 | Smith et al. | |
| 7,407,074 B2 | 8/2008 | Ortiz et al. | |
| 7,419,495 B2 | 9/2008 | Menn et al. | |

(56) References Cited

U.S. PATENT DOCUMENTS

| | | |
|---|---|---|
| 7,422,137 B2 | 9/2008 | Manzo |
| 7,431,724 B2 | 10/2008 | Manetakis et al. |
| 7,452,327 B2 | 11/2008 | Durgin et al. |
| 7,485,124 B2 | 2/2009 | Kuhns et al. |
| 7,488,335 B2 | 2/2009 | Sgro |
| 7,510,562 B2 | 3/2009 | Lindsay |
| 7,552,853 B2 | 6/2009 | Mas et al. |
| 7,559,937 B2 | 7/2009 | de la Torre et al. |
| 7,572,266 B2 | 8/2009 | Young et al. |
| 7,578,827 B2 | 8/2009 | Gadberry et al. |
| 7,582,095 B2 | 9/2009 | Shipp et al. |
| 7,585,304 B2 | 9/2009 | Hughett |
| 7,615,058 B2 | 11/2009 | Sixto, Jr. et al. |
| 7,615,060 B2 | 11/2009 | Stokes et al. |
| 7,621,926 B2 | 11/2009 | Wixey et al. |
| 7,637,917 B2 | 12/2009 | Whitfield et al. |
| 7,644,848 B2 | 1/2010 | Swayze et al. |
| 7,686,820 B2 | 3/2010 | Huitema et al. |
| 7,695,482 B2 | 4/2010 | Viola |
| 7,717,926 B2 | 5/2010 | Whitfield et al. |
| 7,727,247 B2 | 6/2010 | Kimura et al. |
| 7,727,248 B2 | 6/2010 | Smith et al. |
| 7,731,724 B2 | 6/2010 | Huitema et al. |
| 7,731,725 B2 | 6/2010 | Gadberry et al. |
| 7,736,388 B2 | 6/2010 | Goldfarb et al. |
| 7,740,639 B2 | 6/2010 | Hummel et al. |
| 7,740,641 B2 | 6/2010 | Huitema |
| 7,744,623 B2 | 6/2010 | Anderson |
| 7,752,853 B2 | 7/2010 | Singh et al. |
| 7,753,250 B2 | 7/2010 | Clauson et al. |
| 7,766,207 B2 | 8/2010 | Mather et al. |
| 7,766,925 B2 | 8/2010 | Stokes et al. |
| 7,770,773 B2 | 8/2010 | Whitman et al. |
| 7,776,058 B2 | 8/2010 | Rosenberg et al. |
| 7,780,688 B2 | 8/2010 | Sakakine et al. |
| 7,793,813 B2 | 9/2010 | Bettuchi |
| 7,806,903 B2 | 10/2010 | Shibata et al. |
| 7,819,886 B2 | 10/2010 | Whitfield et al. |
| 7,823,592 B2 | 11/2010 | Bettuchi et al. |
| 7,857,828 B2 | 12/2010 | Jabba et al. |
| 7,871,416 B2 | 1/2011 | Phillips |
| 7,875,029 B1 | 1/2011 | Hausen |
| 7,887,553 B2 | 2/2011 | Lehman et al. |
| 7,887,554 B2 | 2/2011 | Stokes et al. |
| 7,892,244 B2 | 2/2011 | Monassevitch et al. |
| 7,896,895 B2 | 3/2011 | Boudreaux et al. |
| 7,901,420 B2 | 3/2011 | Dunn |
| 7,905,890 B2 | 3/2011 | Whitfield et al. |
| 7,914,544 B2 | 3/2011 | Nguyen et al. |
| 7,914,551 B2 | 3/2011 | Ortiz et al. |
| 7,942,890 B2 | 5/2011 | D'Agostino et al. |
| 7,947,052 B2 | 5/2011 | Baxter, III et al. |
| 7,954,682 B2 | 6/2011 | Giordano et al. |
| 7,963,433 B2 | 6/2011 | Whitman et al. |
| 7,967,831 B2 | 6/2011 | Rosenberg et al. |
| 7,988,027 B2 | 8/2011 | Olson et al. |
| 7,998,155 B2 | 8/2011 | Manzo |
| 8,011,550 B2 | 9/2011 | Aranyi et al. |
| 8,011,555 B2 | 9/2011 | Tarinelli et al. |
| 8,016,178 B2 | 9/2011 | Olson et al. |
| 8,021,375 B2 | 9/2011 | Aldrich et al. |
| 8,021,378 B2 | 9/2011 | Sixto, Jr. et al. |
| 8,038,686 B2 | 10/2011 | Huitema et al. |
| 8,048,088 B2 | 11/2011 | Green et al. |
| 8,056,565 B2 | 11/2011 | Zergiebel |
| 8,062,310 B2 | 11/2011 | Shibata et al. |
| 8,062,311 B2 | 11/2011 | Litscher et al. |
| 8,062,314 B2 | 11/2011 | Sixto, Jr. et al. |
| 8,066,720 B2 | 11/2011 | Knodel et al. |
| 8,066,721 B2 | 11/2011 | Kortenbach et al. |
| 8,066,722 B2 | 11/2011 | Miyagi et al. |
| 8,070,760 B2 | 12/2011 | Fujita |
| 8,074,857 B2 | 12/2011 | Peterson et al. |
| 8,075,571 B2 | 12/2011 | Vitali et al. |
| 8,080,021 B2 | 12/2011 | Griego |
| 8,083,668 B2 | 12/2011 | Durgin et al. |
| 8,088,061 B2 | 1/2012 | Wells et al. |
| 8,091,755 B2 | 1/2012 | Kayan et al. |
| 8,100,926 B1 | 1/2012 | Filshie et al. |
| 8,128,643 B2 | 3/2012 | Aranyi et al. |
| 8,133,240 B2 | 3/2012 | Damarati |
| 8,137,368 B2 | 3/2012 | Kayan et al. |
| 8,142,451 B2 | 3/2012 | Boulnois et al. |
| 8,157,145 B2 | 4/2012 | Shelton, IV et al. |
| 8,157,149 B2 | 4/2012 | Olson et al. |
| 8,157,151 B2 | 4/2012 | Ingmanson et al. |
| 8,172,859 B2 | 5/2012 | Matsuno et al. |
| 8,172,870 B2 | 5/2012 | Shipp |
| 8,177,797 B2 | 5/2012 | Shimoji et al. |
| 8,182,529 B2 | 5/2012 | Gordon et al. |
| 8,187,290 B2 | 5/2012 | Buckman et al. |
| 8,192,449 B2 | 6/2012 | Maier et al. |
| 8,211,119 B2 | 7/2012 | Palmer et al. |
| 8,211,120 B2 | 7/2012 | Itoh |
| 8,211,124 B2 | 7/2012 | Ainsworth et al. |
| 8,216,255 B2 | 7/2012 | Smith et al. |
| 8,216,257 B2 | 7/2012 | Huitema et al. |
| 8,236,012 B2 | 8/2012 | Molitor et al. |
| 8,241,322 B2 | 8/2012 | Whitman et al. |
| 8,246,634 B2 | 8/2012 | Huitema et al. |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino et al. |
| 8,267,945 B2 | 9/2012 | Nguyen et al. |
| 8,267,946 B2 | 9/2012 | Whitfield et al. |
| 8,272,554 B2 | 9/2012 | Whitman et al. |
| 8,282,655 B2 | 10/2012 | Whitfield et al. |
| 8,287,559 B2 | 10/2012 | Barker et al. |
| 8,308,743 B2 | 11/2012 | Matsuno et al. |
| 8,313,497 B2 | 11/2012 | Walberg et al. |
| 8,328,822 B2 | 12/2012 | Huitema et al. |
| 8,336,556 B2 | 12/2012 | Zergiebel |
| 8,348,130 B2 | 1/2013 | Shah et al. |
| 8,357,171 B2 | 1/2013 | Whitfield et al. |
| 8,366,709 B2 | 2/2013 | Schechter et al. |
| 8,366,726 B2 | 2/2013 | Dennis |
| 8,371,491 B2 | 2/2013 | Huitema et al. |
| 8,372,095 B2 | 2/2013 | Viola |
| 8,382,773 B2 | 2/2013 | Whitfield et al. |
| 8,398,655 B2 | 3/2013 | Cheng et al. |
| 8,403,138 B2 | 3/2013 | Weisshaupt et al. |
| 8,403,945 B2 | 3/2013 | Whitfield et al. |
| 8,403,946 B2 | 3/2013 | Whitfield et al. |
| 8,408,442 B2 | 4/2013 | Racenet et al. |
| 8,409,222 B2 | 4/2013 | Whitfield et al. |
| 8,409,223 B2 | 4/2013 | Sorrentino et al. |
| 8,419,752 B2 | 4/2013 | Sorrentino et al. |
| 8,430,892 B2 | 4/2013 | Bindra et al. |
| 8,444,660 B2 | 5/2013 | Adams et al. |
| 8,465,460 B2 | 6/2013 | Yodfat et al. |
| 8,465,502 B2 | 6/2013 | Zergiebel |
| 8,475,473 B2 | 7/2013 | Vandenbroek et al. |
| 8,480,688 B2 | 7/2013 | Boulnois et al. |
| 8,486,091 B2 | 7/2013 | Sorrentino et al. |
| 8,491,608 B2 | 7/2013 | Sorrentino et al. |
| 8,496,673 B2 | 7/2013 | Nguyen et al. |
| 8,506,580 B2 | 8/2013 | Zergiebel et al. |
| 8,512,357 B2 | 8/2013 | Viola |
| 8,518,055 B1 | 8/2013 | Cardinale et al. |
| 8,523,882 B2 | 9/2013 | Huitema et al. |
| 8,529,585 B2 | 9/2013 | Jacobs et al. |
| 8,529,586 B2 | 9/2013 | Rosenberg et al. |
| 8,529,588 B2 | 9/2013 | Ahlberg et al. |
| 8,545,486 B2 | 10/2013 | Malkowski |
| 8,545,519 B2 | 10/2013 | Aguirre et al. |
| 8,556,920 B2 | 10/2013 | Huitema et al. |
| 8,568,430 B2 | 10/2013 | Shipp |
| 8,579,918 B2 | 11/2013 | Whitfield et al. |
| 8,585,716 B2 | 11/2013 | Roskopf et al. |
| 8,585,717 B2 | 11/2013 | Sorrentino et al. |
| 8,603,109 B2 | 12/2013 | Aranyi et al. |
| 8,623,044 B2 | 1/2014 | Timm et al. |
| 8,628,547 B2 | 1/2014 | Weller et al. |

(56) References Cited

U.S. PATENT DOCUMENTS

| | | |
|---|---|---|
| 8,632,520 B2 | 1/2014 | Otley |
| 8,636,191 B2 | 1/2014 | Meagher |
| 8,652,151 B2 | 2/2014 | Lehman et al. |
| 8,652,152 B2 | 2/2014 | Aranyi et al. |
| 8,663,247 B2 | 3/2014 | Menn et al. |
| 8,685,048 B2 | 4/2014 | Adams et al. |
| 8,690,899 B2 | 4/2014 | Kogiso et al. |
| 8,708,210 B2 | 4/2014 | Zemlok et al. |
| 8,708,213 B2 | 4/2014 | Shelton, IV et al. |
| 8,709,027 B2 | 4/2014 | Adams et al. |
| 8,715,299 B2 | 5/2014 | Menn et al. |
| 8,720,766 B2 | 5/2014 | Hess et al. |
| 8,734,469 B2 | 5/2014 | Pribanic et al. |
| 8,747,423 B2 | 6/2014 | Whitfield et al. |
| 8,753,356 B2 | 6/2014 | Vitali et al. |
| 8,758,392 B2 | 6/2014 | Crainich |
| 8,771,169 B2 | 7/2014 | Whitman et al. |
| 8,795,302 B2 | 8/2014 | Wild |
| 8,808,310 B2 | 8/2014 | Jones et al. |
| 8,814,884 B2 | 8/2014 | Whitfield et al. |
| 8,821,516 B2 | 9/2014 | Huitema |
| 8,839,954 B2 | 9/2014 | Disch |
| 8,845,659 B2 | 9/2014 | Whitfield et al. |
| 8,894,665 B2 | 11/2014 | Sorrentino et al. |
| 8,894,666 B2 | 11/2014 | Schulz et al. |
| 8,900,253 B2 | 12/2014 | Aranyi et al. |
| 8,915,930 B2 | 12/2014 | Huitema et al. |
| 8,915,931 B2 | 12/2014 | Boudreaux et al. |
| 8,939,974 B2 | 1/2015 | Boudreaux et al. |
| 8,945,151 B2 | 2/2015 | Salas |
| 8,950,646 B2 | 2/2015 | Viola |
| 8,968,337 B2 | 3/2015 | Whitfield et al. |
| 8,968,342 B2 | 3/2015 | Wingardner, III et al. |
| 8,973,804 B2 | 3/2015 | Hess et al. |
| 8,986,343 B2 | 3/2015 | Bourque et al. |
| 8,998,935 B2 | 4/2015 | Hart |
| 9,011,464 B2 | 4/2015 | Zammataro |
| 9,011,465 B2 | 4/2015 | Whitfield et al. |
| 9,028,511 B2 | 5/2015 | Weller et al. |
| 9,060,779 B2 | 6/2015 | Martinez |
| 9,084,604 B2 | 7/2015 | Litscher et al. |
| 9,089,334 B2 | 7/2015 | Sorrentino et al. |
| 9,113,892 B2 | 8/2015 | Malkowski et al. |
| 9,113,893 B2 | 8/2015 | Sorrentino et al. |
| 9,119,629 B2 | 9/2015 | Cardinale et al. |
| 9,186,136 B2 | 11/2015 | Malkowski et al. |
| 9,186,153 B2 | 11/2015 | Zammataro |
| 9,208,429 B2 | 12/2015 | Thornton et al. |
| 9,220,507 B1 | 12/2015 | Patel et al. |
| 9,226,825 B2 | 1/2016 | Starksen et al. |
| 9,232,947 B2 | 1/2016 | Brenner et al. |
| 9,265,486 B2 | 2/2016 | Hughett, Sr. et al. |
| 9,271,737 B2 | 3/2016 | Castro et al. |
| 9,282,972 B1 | 3/2016 | Patel et al. |
| 9,282,973 B2 | 3/2016 | Hughett, Sr. et al. |
| 9,327,890 B1* | 5/2016 | Connelly .............. B65D 71/70 |
| 9,358,011 B2 | 6/2016 | Sorrentino et al. |
| 9,364,216 B2 | 6/2016 | Rockrohr et al. |
| 9,364,240 B2 | 6/2016 | Whitfield et al. |
| 9,370,400 B2 | 6/2016 | Parihar |
| 9,393,024 B2 | 7/2016 | Whitfield et al. |
| 9,408,610 B2 | 8/2016 | Hartoumbekis |
| 9,414,844 B2 | 8/2016 | Zergiebel et al. |
| 9,433,411 B2 | 9/2016 | Racenet et al. |
| 9,433,422 B2 | 9/2016 | Crainich et al. |
| 9,439,654 B2 | 9/2016 | Sorrentino et al. |
| 9,445,810 B2 | 9/2016 | Cappola |
| 9,445,820 B2 | 9/2016 | Whiting |
| 9,456,824 B2 | 10/2016 | Willett et al. |
| 9,468,444 B2 | 10/2016 | Menn et al. |
| 9,480,477 B2 | 11/2016 | Aranyi et al. |
| 9,480,480 B2 | 11/2016 | Santilli et al. |
| 9,486,225 B2 | 11/2016 | Michler et al. |
| 9,498,227 B2 | 11/2016 | Zergiebel et al. |
| 9,504,472 B2 | 11/2016 | Kamler |
| 9,517,064 B2 | 12/2016 | Sarradon |
| 9,526,501 B2 | 12/2016 | Malkowski |
| 9,526,565 B2 | 12/2016 | Strobl |
| 9,532,787 B2 | 1/2017 | Zammataro |
| 9,545,254 B2 | 1/2017 | Sorrentino et al. |
| 9,549,741 B2 | 1/2017 | Zergiebel |
| 9,561,038 B2 | 2/2017 | Shelton, IV et al. |
| 9,566,066 B2 | 2/2017 | Kasvikis |
| 9,597,089 B2 | 3/2017 | Menn |
| 9,642,627 B2 | 5/2017 | Zammataro |
| 9,681,877 B2 | 6/2017 | Blake, III et al. |
| 9,687,247 B2 | 6/2017 | Aranyi et al. |
| 9,700,324 B2 | 7/2017 | Mazzucco et al. |
| 9,717,504 B2 | 8/2017 | Huitema |
| 9,717,505 B2 | 8/2017 | Whitfield et al. |
| 9,724,163 B2 | 8/2017 | Orban |
| 9,737,310 B2 | 8/2017 | Whitfield et al. |
| 9,750,500 B2 | 9/2017 | Malkowski |
| 9,763,668 B2 | 9/2017 | Whitfield et al. |
| 9,763,669 B2 | 9/2017 | Griego |
| 9,775,623 B2 | 10/2017 | Zammataro et al. |
| 9,775,624 B2 | 10/2017 | Rockrohr et al. |
| 9,782,164 B2 | 10/2017 | Mumaw et al. |
| 9,782,181 B2 | 10/2017 | Vitali et al. |
| 9,808,257 B2 | 11/2017 | Armenteros et al. |
| 9,848,886 B2 | 12/2017 | Malkowski et al. |
| 9,855,043 B2 | 1/2018 | Malkowski |
| 9,883,866 B2 | 2/2018 | Roundy et al. |
| 9,931,124 B2 | 4/2018 | Gokharu |
| 9,968,361 B2 | 5/2018 | Aranyi et al. |
| 9,968,362 B2 | 5/2018 | Malkowski et al. |
| 10,004,502 B2 | 6/2018 | Malkowski et al. |
| 10,136,939 B2 | 11/2018 | Minnelli et al. |
| 10,159,484 B2 | 12/2018 | Sorrentino et al. |
| 10,159,491 B2 | 12/2018 | Gokharu |
| 10,159,492 B2 | 12/2018 | Zammataro |
| 10,166,027 B2 | 1/2019 | Aranyi et al. |
| 10,231,732 B1 | 3/2019 | Racenet et al. |
| 10,231,735 B2 | 3/2019 | Sorrentino et al. |
| 10,231,738 B2 | 3/2019 | Sorrentino et al. |
| 10,258,346 B2 | 4/2019 | Zergiebel et al. |
| 10,292,712 B2 | 5/2019 | Shankarsetty |
| 10,349,936 B2 | 7/2019 | Rockrohr et al. |
| 10,349,950 B2 | 7/2019 | Aranyi et al. |
| 10,357,250 B2 | 7/2019 | Zammataro |
| 10,363,045 B2 | 7/2019 | Whitfield et al. |
| 10,368,876 B2 | 8/2019 | Bhatnagar et al. |
| 10,390,831 B2 | 8/2019 | Holsten et al. |
| 10,426,489 B2 | 10/2019 | Baril |
| 2002/0046961 A1* | 4/2002 | Levinson ............ A61B 17/1222 206/339 |
| 2002/0123742 A1 | 9/2002 | Baxter et al. |
| 2003/0014060 A1 | 1/2003 | Wilson et al. |
| 2003/0114867 A1 | 6/2003 | Bolduc et al. |
| 2003/0208231 A1 | 11/2003 | Williamson et al. |
| 2003/0229360 A1 | 12/2003 | Gayton |
| 2004/0040875 A1* | 3/2004 | Gallagher .......... A61B 17/1222 206/399 |
| 2004/0097970 A1 | 5/2004 | Hughett |
| 2004/0097971 A1 | 5/2004 | Hughett |
| 2004/0133215 A1 | 7/2004 | Baxter |
| 2004/0138681 A1 | 7/2004 | Pier |
| 2004/0167545 A1 | 8/2004 | Sadler et al. |
| 2004/0176783 A1 | 9/2004 | Edoga et al. |
| 2004/0176784 A1 | 9/2004 | Okada |
| 2004/0193213 A1 | 9/2004 | Aranyi et al. |
| 2004/0232197 A1 | 11/2004 | Shelton et al. |
| 2005/0010242 A1 | 1/2005 | Lindsay |
| 2005/0090837 A1 | 4/2005 | Sixto et al. |
| 2005/0096670 A1 | 5/2005 | Wellman et al. |
| 2005/0096671 A1 | 5/2005 | Wellman et al. |
| 2005/0107810 A1 | 5/2005 | Morales et al. |
| 2005/0107811 A1 | 5/2005 | Starksen et al. |
| 2005/0107871 A1 | 5/2005 | Realyvasquez et al. |
| 2005/0125010 A1 | 6/2005 | Smith et al. |
| 2005/0149068 A1 | 7/2005 | Williams et al. |
| 2005/0149069 A1 | 7/2005 | Bertolero et al. |
| 2005/0171560 A1 | 8/2005 | Hughett |
| 2005/0175703 A1 | 8/2005 | Hunter et al. |

(56) References Cited

U.S. PATENT DOCUMENTS

| | | |
|---|---|---|
| 2005/0177176 A1 | 8/2005 | Gerbi et al. |
| 2005/0216036 A1 | 9/2005 | Nakao |
| 2005/0216056 A1 | 9/2005 | Valdevit et al. |
| 2005/0222665 A1 | 10/2005 | Aranyi |
| 2005/0228416 A1 | 10/2005 | Burbank et al. |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2006/0000867 A1 | 1/2006 | Shelton et al. |
| 2006/0004388 A1 | 1/2006 | Whayne et al. |
| 2006/0009789 A1 | 1/2006 | Gambale et al. |
| 2006/0009790 A1 | 1/2006 | Blake et al. |
| 2006/0009792 A1 | 1/2006 | Baker et al. |
| 2006/0020271 A1 | 1/2006 | Stewart et al. |
| 2006/0079115 A1 | 4/2006 | Aranyi |
| 2006/0085015 A1 | 4/2006 | Whitfield et al. |
| 2006/0085021 A1 | 4/2006 | Wenzler |
| 2006/0100649 A1 | 5/2006 | Hart |
| 2006/0124485 A1* | 6/2006 | Kennedy ............ A61B 17/1222 206/340 |
| 2006/0163312 A1 | 7/2006 | Viola et al. |
| 2006/0173470 A1 | 8/2006 | Oray et al. |
| 2006/0190013 A1 | 8/2006 | Menn |
| 2006/0217749 A1 | 9/2006 | Wilson et al. |
| 2006/0224165 A1 | 10/2006 | Surti et al. |
| 2006/0224170 A1 | 10/2006 | Duff |
| 2006/0235439 A1 | 10/2006 | Molitor et al. |
| 2006/0241655 A1 | 10/2006 | Viola |
| 2006/0259045 A1 | 11/2006 | Damarati |
| 2006/0259049 A1 | 11/2006 | Harada et al. |
| 2007/0021766 A1 | 1/2007 | Belagali et al. |
| 2007/0038233 A1 | 2/2007 | Martinez et al. |
| 2007/0049947 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0083218 A1 | 4/2007 | Morris |
| 2007/0093790 A1 | 4/2007 | Downey et al. |
| 2007/0112365 A1 | 5/2007 | Hilal et al. |
| 2007/0118161 A1 | 5/2007 | Kennedy et al. |
| 2007/0118174 A1 | 5/2007 | Chu |
| 2007/0173866 A1 | 7/2007 | Sorrentino et al. |
| 2007/0185504 A1 | 8/2007 | Manetakis et al. |
| 2007/0191868 A1 | 8/2007 | Theroux et al. |
| 2007/0203510 A1 | 8/2007 | Bettuchi |
| 2007/0276417 A1 | 11/2007 | Mendes, Jr. et al. |
| 2007/0282355 A1 | 12/2007 | Brown et al. |
| 2007/0288039 A1 | 12/2007 | Aranyi et al. |
| 2007/0293875 A1 | 12/2007 | Soetikno et al. |
| 2008/0004636 A1 | 1/2008 | Walberg et al. |
| 2008/0045981 A1 | 2/2008 | Margolin et al. |
| 2008/0051808 A1 | 2/2008 | Rivera et al. |
| 2008/0103510 A1 | 5/2008 | Taylor et al. |
| 2008/0147092 A1 | 6/2008 | Rogge et al. |
| 2008/0167665 A1 | 7/2008 | Arp et al. |
| 2008/0228199 A1 | 9/2008 | Cropper et al. |
| 2008/0255413 A1 | 10/2008 | Zemlok et al. |
| 2008/0255589 A1 | 10/2008 | Blakeney et al. |
| 2008/0306492 A1 | 12/2008 | Shibata et al. |
| 2008/0306493 A1 | 12/2008 | Shibata et al. |
| 2008/0312670 A1 | 12/2008 | Lutze et al. |
| 2009/0088783 A1 | 4/2009 | Kennedy et al. |
| 2009/0182193 A1 | 7/2009 | Whitman et al. |
| 2009/0204115 A1 | 8/2009 | Dees, Jr. et al. |
| 2009/0209946 A1 | 8/2009 | Swayze et al. |
| 2009/0228023 A1 | 9/2009 | Cui |
| 2009/0261142 A1 | 10/2009 | Milliman et al. |
| 2009/0264904 A1 | 10/2009 | Aldrich et al. |
| 2009/0312775 A1 | 12/2009 | Gilkey et al. |
| 2009/0326558 A1 | 12/2009 | Cui et al. |
| 2010/0089970 A1 | 4/2010 | Smith et al. |
| 2010/0274264 A1 | 10/2010 | Schulz et al. |
| 2010/0318103 A1 | 12/2010 | Cheng et al. |
| 2010/0331862 A1 | 12/2010 | Monassevitch et al. |
| 2011/0054498 A1 | 3/2011 | Monassevitch et al. |
| 2011/0087220 A1 | 4/2011 | Felder et al. |
| 2011/0087244 A1* | 4/2011 | Weisshaupt .......... A61B 17/122 606/143 |
| 2011/0087268 A1 | 4/2011 | Livneh |
| 2011/0144662 A1 | 6/2011 | McLawhorn et al. |
| 2011/0208211 A1 | 8/2011 | Whitfield et al. |
| 2011/0208212 A1 | 8/2011 | Zergiebel et al. |
| 2011/0218554 A1 | 9/2011 | Cheng et al. |
| 2011/0224700 A1 | 9/2011 | Schmidt et al. |
| 2011/0295290 A1 | 12/2011 | Whitfield |
| 2011/0313437 A1 | 12/2011 | Yeh |
| 2012/0022526 A1 | 1/2012 | Aldridge et al. |
| 2012/0046671 A1 | 2/2012 | Matsuoka et al. |
| 2012/0048759 A1 | 3/2012 | Disch et al. |
| 2012/0053402 A1 | 3/2012 | Conlon et al. |
| 2012/0226291 A1 | 9/2012 | Malizia et al. |
| 2012/0253298 A1 | 10/2012 | Henderson et al. |
| 2012/0265220 A1 | 10/2012 | Menn |
| 2012/0330326 A1 | 12/2012 | Creston et al. |
| 2013/0041379 A1 | 2/2013 | Bodor et al. |
| 2013/0131697 A1 | 5/2013 | Hartoumbekis |
| 2013/0161216 A1* | 6/2013 | Disch ................... B65D 85/24 206/339 |
| 2013/0165951 A1 | 6/2013 | Blake, III |
| 2013/0172909 A1 | 7/2013 | Harris |
| 2013/0172910 A1 | 7/2013 | Malkowski |
| 2013/0175320 A1 | 7/2013 | Mandakolathur Vasudevan et al. |
| 2013/0226200 A1 | 8/2013 | Kappel et al. |
| 2013/0253540 A1 | 9/2013 | Castro et al. |
| 2013/0325057 A1 | 12/2013 | Larson et al. |
| 2014/0054192 A1* | 2/2014 | Chancibot ............ B65D 75/326 206/438 |
| 2014/0074143 A1 | 3/2014 | Fitzgerald et al. |
| 2014/0188159 A1 | 7/2014 | Steege |
| 2014/0263565 A1 | 9/2014 | Lytle, IV et al. |
| 2014/0276970 A1 | 9/2014 | Messerly et al. |
| 2014/0371728 A1 | 12/2014 | Vaughn |
| 2015/0032131 A1 | 1/2015 | Sorrentino et al. |
| 2015/0201953 A1 | 7/2015 | Strobl et al. |
| 2015/0265282 A1 | 9/2015 | Miles et al. |
| 2015/0313452 A1 | 11/2015 | Hasser et al. |
| 2015/0314451 A1 | 11/2015 | Nixon |
| 2016/0004956 A1 | 1/2016 | Reynolds et al. |
| 2016/0030044 A1 | 2/2016 | Zammataro |
| 2016/0113655 A1 | 4/2016 | Holsten |
| 2016/0151071 A1 | 6/2016 | Tokarz et al. |
| 2016/0213377 A1 | 7/2016 | Shankarsetty |
| 2016/0242767 A1 | 8/2016 | Kasvikis |
| 2016/0242789 A1 | 8/2016 | Sorrentino et al. |
| 2016/0256157 A1 | 9/2016 | Rockrohr et al. |
| 2016/0256158 A1 | 9/2016 | Whitfield et al. |
| 2016/0262764 A1 | 9/2016 | Gokharu |
| 2016/0296236 A1 | 10/2016 | Whitfield et al. |
| 2016/0338695 A1 | 11/2016 | Hartoumbekis |
| 2016/0338699 A1 | 11/2016 | Sorrentino et al. |
| 2017/0027581 A1 | 2/2017 | Zergiebel et al. |
| 2017/0049449 A1 | 2/2017 | Aranyi et al. |
| 2017/0065277 A1 | 3/2017 | Malkowski |
| 2017/0065281 A1 | 3/2017 | Zammataro |
| 2017/0086846 A1 | 3/2017 | Sorrentino et al. |
| 2017/0086850 A1 | 3/2017 | Zergiebel |
| 2017/0128071 A1 | 5/2017 | Holsten et al. |
| 2017/0172780 A1 | 6/2017 | Murthy Aravalli |
| 2017/0202567 A1 | 7/2017 | Griffiths et al. |
| 2017/0238936 A1 | 8/2017 | Mujawar |
| 2017/0245921 A1 | 8/2017 | Joseph et al. |
| 2017/0252042 A1 | 9/2017 | Kethman et al. |
| 2017/0258472 A1 | 9/2017 | Aranyi et al. |
| 2017/0290587 A1 | 10/2017 | Schober et al. |
| 2017/0325814 A1 | 11/2017 | Malkowski |
| 2017/0340325 A1 | 11/2017 | Baril et al. |
| 2017/0340331 A1 | 11/2017 | Hu et al. |
| 2017/0340332 A1 | 11/2017 | Whitfield et al. |
| 2017/0360449 A1 | 12/2017 | Rockrohr et al. |
| 2018/0008276 A1 | 1/2018 | Bhatnagar et al. |
| 2018/0008277 A1 | 1/2018 | Baril |

(56) References Cited

U.S. PATENT DOCUMENTS

| | | |
|---|---|---|
| 2018/0021041 A1 | 1/2018 | Zhang et al. |
| 2018/0070952 A1 | 3/2018 | Malkowski et al. |
| 2018/0116671 A1 | 5/2018 | Prior |
| 2018/0116673 A1 | 5/2018 | Baril et al. |
| 2018/0116674 A1 | 5/2018 | Baril |
| 2018/0116675 A1 | 5/2018 | Baril |
| 2018/0116676 A1 | 5/2018 | Williams |
| 2018/0168660 A1 | 6/2018 | Gokharu |
| 2018/0214156 A1 | 8/2018 | Baril et al. |
| 2018/0221028 A1 | 8/2018 | Williams |
| 2018/0228492 A1 | 8/2018 | Aranyi et al. |
| 2018/0228567 A1 | 8/2018 | Baril et al. |
| 2018/0235632 A1 | 8/2018 | Mujawar et al. |
| 2018/0235633 A1 | 8/2018 | Baril et al. |
| 2018/0235637 A1 | 8/2018 | Xu et al. |
| 2018/0242977 A1 | 8/2018 | Tan et al. |
| 2018/0263624 A1 | 9/2018 | Malkowski et al. |
| 2018/0271526 A1 | 9/2018 | Zammataro |
| 2018/0317927 A1 | 11/2018 | Cal et al. |
| 2018/0317928 A1 | 11/2018 | P V R |
| 2018/0325519 A1 | 11/2018 | Baril et al. |
| 2019/0000449 A1 | 1/2019 | Baril et al. |
| 2019/0000482 A1 | 1/2019 | Hu et al. |
| 2019/0000584 A1 | 1/2019 | Baril |
| 2019/0021738 A1 | 1/2019 | Hartoumbekis |
| 2019/0038375 A1 | 2/2019 | Baril et al. |
| 2019/0046202 A1 | 2/2019 | Baril et al. |
| 2019/0046203 A1 | 2/2019 | Baril et al. |
| 2019/0046207 A1 | 2/2019 | Czernik et al. |
| 2019/0046208 A1 | 2/2019 | Baril et al. |
| 2019/0053806 A1 | 2/2019 | Zhang et al. |
| 2019/0053808 A1 | 2/2019 | Baril et al. |
| 2019/0059904 A1 | 2/2019 | Zammataro |
| 2019/0076147 A1 | 3/2019 | Baril et al. |
| 2019/0076148 A1 | 3/2019 | Baril et al. |
| 2019/0076149 A1 | 3/2019 | Baril et al. |
| 2019/0076150 A1 | 3/2019 | Gokharu |
| 2019/0076210 A1 | 3/2019 | Baril et al. |
| 2019/0133583 A1 | 5/2019 | Baril et al. |
| 2019/0133584 A1 | 5/2019 | Baril et al. |
| 2019/0133593 A1 | 5/2019 | P V R |
| 2019/0133594 A1 | 5/2019 | Dinino et al. |
| 2019/0133595 A1 | 5/2019 | Baril et al. |
| 2019/0150935 A1 | 5/2019 | Raikar et al. |
| 2019/0175176 A1 | 6/2019 | Zammataro |
| 2019/0175187 A1 | 6/2019 | P V R |
| 2019/0175188 A1 | 6/2019 | P V R |
| 2019/0175189 A1 | 6/2019 | P V R |
| 2019/0192139 A1 | 6/2019 | Rockrohr et al. |
| 2019/0209177 A1 | 7/2019 | Whitfield et al. |
| 2019/0216464 A1 | 7/2019 | Baril et al. |
| 2019/0239893 A1 | 8/2019 | Shankarsetty |

FOREIGN PATENT DOCUMENTS

| | | |
|---|---|---|
| CN | 103251441 A | 8/2013 |
| CN | 104605911 B | 2/2017 |
| DE | 202005001664 U1 | 5/2005 |
| DE | 202007003398 U1 | 6/2007 |
| DE | 202009006113 U1 | 7/2009 |
| EP | 0000756 A1 | 2/1979 |
| EP | 0406724 A1 | 1/1991 |
| EP | 0514139 A2 | 11/1992 |
| EP | 0732078 A2 | 9/1996 |
| EP | 1769757 A1 | 4/2007 |
| EP | 3132756 A1 | 2/2017 |
| GB | 2073022 A | 10/1981 |
| JP | 2003033361 A | 2/2003 |
| JP | 2006154230 A | 6/2006 |
| JP | 2006277221 A | 10/2006 |
| JP | 2008017876 A | 1/2008 |
| JP | 2011186812 A | 9/2011 |
| JP | 2013166982 A | 8/2013 |
| WO | 9003763 A1 | 4/1990 |
| WO | 0042922 A1 | 7/2000 |
| WO | 0166001 A2 | 9/2001 |
| WO | 0167965 A1 | 9/2001 |
| WO | 2016192096 A1 | 12/2016 |
| WO | 2016192718 A2 | 12/2016 |
| WO | 2016197350 A1 | 12/2016 |
| WO | 2016206015 A1 | 12/2016 |
| WO | 2017084000 A1 | 5/2017 |
| WO | 2017146138 A1 | 8/2017 |

OTHER PUBLICATIONS

Extended European Search Report corresponding to Patent Application EP 18154617.7 dated Jun. 25, 2018.
Extended European Search Report corresponding to Patent Application EP 18155158.1 dated Jun. 28, 2018.
Extended European Search Report corresponding to Patent Application EP 15877428.1 dated Jul. 2, 2018.
Extended European Search Report corresponding to Patent Application EP 18157789.1 dated Jul. 5, 2018.
Canadian Office Action corresponding to Patent Application CA 2,972,444 dated Aug. 9, 2018.
Extended European Search Report corresponding to Patent Application EP 18156458.4 dated Sep. 3, 2018.
Extended European Search Report corresponding to Patent Application EP 18171682.0 dated Sep. 18, 2018.
Extended European Search Report corresponding to Patent Application EP 15878354.8 dated Sep. 19, 2018.
Extended European Search Report corresponding to Patent Application EP 18183394.8 dated Sep. 28, 2018.
Extended European Search Report corresponding to Patent Application EP 18163041.9 dated Sep. 28, 2018.
Extended European Search Report corresponding to Patent Application EP 18170524.5 dated Oct. 1, 2018.
Japanese Office Action corresponding to Patent Application JP 2017-536546 dated Oct. 15, 2018.
Extended European Search Report corresponding to Patent Application EP 18187640.0 dated Nov. 30, 2018.
Extended European Search Report corresponding to Patent Application EP 18187690.5 dated Nov. 30, 2018.
Chinese First Office Action corresponding to Patent Application CN 201510696298.9 dated Dec. 3, 2018.
Extended European Search Report corresponding to Patent Application EP 18158143.0 dated Dec. 5, 2018.
International Search Report corresponding to Int'l Patent Appln. PCT/US2018/050316 dated Dec. 31, 2018.
International Search Report corresponding to Int'l Patent Appln. PCT/US2018/050336 dated Jan. 7, 2019.
International Search Report corresponding to Int'l Patent Appln. PCT/US2018/050325 dated Jan. 7, 2019.
International Search Report corresponding to Int'l Patent Appln. PCT/US2018/045306 dated Jan. 16, 2019.
International Search Report corresponding to Int'l Patent Appln. PCT/US2018/050349 dated Jan. 21, 2019.
International Search Report corresponding to Int'l Patent Appln. PCT/US2018/045725 dated Jan. 28, 2019.
Extended European Search Report corresponding to European Patent Application EP 18208630.6 dated Feb. 12, 2019.
International Search Report corresponding to Int'l Patent Appln. PCT/US2018/057910 dated Feb. 22, 2019.
International Search Report corresponding to Int'l Patent Appln. PCT/US2018/057922 dated Feb. 22, 2019.
International Search Report corresponding to Int'l Patent Appln. PCT/US2018/058603 dated Feb. 22, 2019.
International Search Report corresponding to Int'l Patent Appln. PCT/US2018/057221 dated Mar. 11, 2019.
Extended European Search Report corresponding to European Patent Application EP 18212043.6 dated Apr. 24, 2019.
Extended European Search Report corresponding to European Patent Application EP 18211565.9 dated Apr. 26, 2019.
Extended European Search Report corresponding to European Patent Application EP 18211921.4 dated Apr. 30, 2019.
Chinese First Office Action corresponding to Chinese Patent Application CN 201510868226.8 dated May 29, 2019.

(56) References Cited

OTHER PUBLICATIONS

Extended European Search Report corresponding to European Patent Application EP 15905685.2 dated May 29, 2019.
European Office Action corresponding to European Patent Application EP 17157606.9 dated Jul. 2, 2019.
Extended European Search Report corresponding to European Patent Application EP 15908025.8 dated Jul. 2, 2019.
Extended European Search Report corresponding to European Patent Application EP 18212054.3 dated Jul. 3, 2019.
Partial Supplementary European Search Report corresponding to European Patent Application EP 16884297.9 dated Jul. 30, 2019.
European Office Action corresponding to EP 12 152 989.5 dated May 4, 2015.
Australian Office Action corresponding to AU 2009212759 dated May 7, 2015.
Chinese Office Action corresponding to Int'l Appln No. CN 201210212642.9 dated Jun. 3, 2015.
European Office Action corresponding to Int'l Appln No. EP 04 719 757.9 dated Jun. 12, 2015.
European Office Action corresponding to Int'l Appln No. EP 13 166 382.5 dated Jun. 19, 2015.
Japanese Office Action corresponding to Int'l Application No. JP 2010-226908 dated Jun. 26, 2015.
Extended European Search Report corresponding to Int'l Application No. EP 15 15 5024.1 dated Jul. 17, 2015.
Extended European Search Report corresponding to Int'l Application No. EP 14 19 2026.4 dated Jul. 17, 2015.
Japanese Office Action corresponding to Int'l Application No. JP 2011-160126 dated Aug. 10, 2015.
Extended European Search Report corresponding to Int'l Application No. EP 14 15 0321.9 dated Sep. 23, 2015.
Extended European Search Report corresponding to Int'l Application No. EP 11 25 0675.3 dated Oct. 7, 2015.
Extended European Search Report corresponding to Int'l Application No. EP 11 25 0674.6 dated Oct. 7, 2015.
Extended European Search Report corresponding to Int'l Application No. EP 12 19 3447.5 dated Oct. 19, 2015.
Canadian Office Action corresponding to Int'l Application No. CA 2,675,875 dated Oct. 26, 2015.
Japanese Office Action corresponding to Int'l Application No. JP 2015-005629 dated Oct. 28, 2015.
Japanese Office Action corresponding to Int'l Application No. JP 2014-245081 dated Oct. 28, 2015.
Canadian Office Action corresponding to Int'l Application No. CA 2,675,921 dated Oct. 30, 2015.
Chinese Office Action corresponding to Int'l Application No. CN 201210555570.8 dated Nov. 2, 2015.
Canadian Office Action corresponding to Int'l Application No. CA 2,676,309 dated Nov. 3, 2015.
Canadian Office Action corresponding to Int'l Application No. CA 2,676,211 dated Nov. 24, 2015.
Canadian Office Action corresponding to Int'l Application No. CA 2,676,547 dated Nov. 25, 2015.
Extended European Search Report corresponding to Int'l Application No. EP 15 17 3809.3 dated Nov. 25, 2015.
Chinese Office Action corresponding to Int'l Application No. CN 201210586814.9 dated Dec. 2, 2015.
Extended European Search Report corresponding to Int'l Application No. EP 12 17 2940.4 dated Dec. 14, 2015.
Chinese First Office Action corresponding to Int'l Appln. No. CN 201210586826.1 dated Dec. 30, 2015.
Extended European Search Report corresponding to Int'l Appln. No. EP 15 18 5362.9 dated Feb. 12, 2016.
Extended European Search Report corresponding to Int'l Appln. No. EP 12 19 7813.4 dated Mar. 7, 2016.
Canadian Office Action corresponding to Int'l Appln. No. CA 2,676,465 dated Mar. 8, 2016.
Japanese Office Action corresponding to Int'l Appln. No. JP 2014-245081 dated Mar. 18, 2016.
Japanese Office Action corresponding to Int'l Appln. No. JP 2015-005629 dated Mar. 18, 2016.
Extended European Search Report corresponding to Int'l Appln. No. EP 15 19 3549.1 dated Mar. 22, 2016.
International Search Report and Written Opinion corresponding to Int'l Appln. No. PCT/CN2015/082199 dated Mar. 31, 2016.
Extended European Search Report corresponding to Int'l Appln. No. EP 15 19 7251.0 dated Apr. 8, 2016.
Extended European Search Report corresponding to Int'l Appln. No. EP 16 15 0739.7 dated May 17, 2016.
Canadian Office Action corresponding to Int'l Appln. No. CA 2,716,672 dated May 31, 2016.
Canadian Office Action corresponding to Int'l Appln. No. CA 2,717,448 dated May 31, 2016.
Canadian Office Action corresponding to Int'l Appln. No. CA 2,721,951 dated Jun. 1, 2016.
Partial European Search Report corresponding to Int'l Appln. No. EP 16 15 0287.7 dated Jun. 16, 2016.
Chinese Second Office Action corresponding to Int'l Appln. No. CN 201210555570.8 dated Jun. 20, 2016.
Chinese First Office Action corresponding to Chinese Appln. No. CN 201410076318.8 dated Jan. 23, 2017.
Extended European Search Report corresponding to European Appln. No. EP 16 18 3184.7 dated Jan. 24, 2017.
Japanese Office Action corresponding to Japanese Appln. No. JP 2016-097807 dated Feb. 14, 2017.
European Office Action corresponding to European Appln. No. EP 12 19 3447.5 dated Apr. 4, 2017.
Chinese First Office Action corresponding to Chinese Appln. No. CN 201410008877.5 dated Apr. 6, 2017.
Extended European Search Report corresponding to European Appln. No. EP 17 15 3714.5 dated May 11, 2017.
Extended European Search Report corresponding to European Appln. No. EP 17 15 8519.3 dated May 19, 2017.
Extended European Search Report corresponding to European Appln. No. EP 17 15 7606.9 dated May 22, 2017.
European Office Action corresponding to European Appln. No. EP 11 25 0674.6 dated May 23, 2017.
Canadian Office Action corresponding to Canadian Appln. No. CA 2,743,402 dated May 30, 2017.
European Office Action corresponding to European Appln. No. EP 16 15 9324.9 dated Aug. 7, 2017.
Chinese First Office Action corresponding to Chinese Appln. No. CN 2014104295806 dated Aug. 31, 2017.
Extended European Search Report corresponding to European Appln. No. EP 17 17 3508.7 dated Sep. 29, 2017.
Chinese Second Office Action corresponding to Chinese Appln. No. CN 201410076318.8 dated Oct. 10, 2017.
Extended European Search Report corresponding to European Appln. No. EP 17 18 0570.8 dated Dec. 6, 2017.
The extended European Search Report corresponding to European Application No. EP 07 25 3905.9, completed Jan. 29, 2008; dated Feb. 7, 2008; (7 Pages).
International Search Report corresponding to International Application No. PCT-US08-58185, completed Sep. 4, 2008; dated Sep. 9, 2008; (2 Pages).
The International Search Report corresponding to International Application No. PCT-US08-59859, completed Sep. 14, 2008; dated Sep. 18, 2008; (2 Pages).
The extended European Search Report corresponding to European Application No. EP 07 25 3807.7, completed Nov. 7, 2008; dated Nov. 26, 2008; (11 Pages).
The extended European Search Report corresponding to European Application No. EP 09 25 2049.3, completed Dec. 11, 2009; dated Jan. 12, 2010; (3 Pages).
The extended European Search Report corresponding to European Application No. EP 09 25 2050.1, completed Dec. 23, 2009; dated Jan. 21, 2010; (3 Pages).
The extended European Search Report corresponding to European Application No. EP 09 25 2051.9, completed Dec. 21, 2009; dated Jan. 28, 2010; (3 Pages).

(56) References Cited

OTHER PUBLICATIONS

The extended European Search Report corresponding to European Application No. EP 09 25 2052.7, completed Nov. 16, 2009; dated Nov. 24, 2009; (3 Pages).
The extended European Search Report corresponding to European Application No. EP 09 25 2053.5, completed Nov. 24, 2009; dated Dec. 1, 2009; (3 Pages).
The extended European Search Report corresponding to European Application No. EP 09 25 2054.3, completed Jan. 7, 2010; dated Jan. 22, 2010; (3 Pages).
The extended European Search Report corresponding to European Application No. EP 09 25 2056.8, completed Jan. 8, 2010; dated Feb. 5, 2010; (3 Pages).
The extended European Search Report corresponding to European Application No. EP 10 25 0497.4, completed May 4, 2010; dated May 12, 2010; (6 Pages).
The extended European Search Report corresponding to European Application No. EP 10 25 2079.8, completed Mar. 8, 2011; dated Mar. 17, 2011; (3 Pages).
The European Search Report corresponding to European Application No. EP 05 81 0218.7, completed Apr. 18, 2011; dated May 20, 2011; (3 pages).
The European Search Report corresponding to European Application No. EP 05 80 7612.6, completed May 2, 2011; dated May 20, 2011; (3 pages).
The extended European Search Report corresponding to European Application No. EP 10 25 1737.2, completed May 9, 2011; dated May 20, 2011; (4 pages).
The extended European Search Report corresponding to European Application No. EP 11 25 0214.1, completed May 25, 2011; dated Jun. 1, 2011; (3 Pages).
The extended European Search Report corresponding to European Application No. EP 11 00 2681.2, completed May 31, 2011; dated Jun. 10, 2011; (3 Pages).
The European Search Report corresponding to European Application No. EP 05 80 2686.5, completed Jan. 9, 2012; dated Jan. 18, 2012; (3 Pages).
The extended European Search Report corresponding to European Application No. EP 12 15 1313.9, completed Mar. 20, 2012 and dated Apr. 12, 2012; (5 Pages).
The extended European Search Report corresponding to European Application No. EP 12 16 1291.5, completed Apr. 24, 2012 and dated May 4, 2012; (5 Pages).
The extended European Search Report corresponding to European Application No. EP 12 16 5891.8, completed Jun. 12, 2012 and dated Jun. 20, 2012; (6 Pages).
The extended European Search Report corresponding to European Application No. EP 12 16 2288.0, completed Jun. 4, 2012 and dated Jul. 7, 2012; (6 Pages).
The extended European Search Report corresponding to European Application No. EP 12 16 4955.2, completed Aug. 23, 2012 and dated Sep. 4, 2012; (5 Pages).
The extended European Search Report corresponding to European Application No. EP 11 25 0754.6, completed Oct. 22, 2012 and dated Oct. 31, 2012; (6 Pages).
The extended European Search Report corresponding to European Application No. EP 12 18 6401.1, completed Nov. 22, 2012 and dated Nov. 30, 2012; (7 Pages).
The extended European Search Report corresponding to European Application No. EP 12 18 6448.2, completed Nov. 28, 2012 and dated Dec. 10, 2012; (6 Pages).
The extended European Search Report corresponding to European Application No. EP 12 19 1706.6, completed Dec. 19, 2012 and dated Jan. 8, 2013; (6 Pages).
The Extended European Search Report corresponding to EP 12 19 8745.7, completed Mar. 19, 2013 and dated Apr. 11, 2013; (8 Pages).
The Extended European Search Report corresponding to EP 12 15 2989.5, completed Apr. 9, 2013 and dated Apr. 18, 2013; (9 Pages).
The Extended European Search Report corresponding to EP 08 73 2820.9, completed Jul. 2, 2013 and dated Jul. 9, 2013; (10 Pages).
The Extended European Search Report corresponding to EP 13 17 2008.8, completed Aug. 14, 2013 and dated Aug. 28, 2013; (8 Pages).
The Extended European Search Report corresponding to EP 13 16 6382.5, completed Nov. 19, 2013 and dated Nov. 28, 2013; (8 Pages).
The Extended European Search Report corresponding to EP 11 25 0194.5, completed Nov. 25, 2013 and dated Dec. 3, 2013; (8 Pages).
The Extended European Search Report corresponding to EP 10 25 1798.4, completed Dec. 12, 2013 and dated Jan. 2, 2014; (9 Pages).
"Salute II Disposable Fixation Device", Technique Guide—Laparoscopic and Open Inguinal and Ventral Hernia Repair; Davol, A Bard Company, 2006; (7 Pages).
The Extended European Search Report corresponding to EP 10 25 2112.7, completed Jul. 29, 2014 and dated Aug. 5, 2014; (8 pp).
The Extended European Search Report corresponding to EP 14 15 1673.2, completed Apr. 25, 2014 and dated May 8, 2014; (8 pp).
Japanese Office Action corresponding to JP 2011-160130 dated Dec. 1, 2014.
Chinese Office Action corresponding to CN 201210015011.8 dated Jan. 4, 2015.
Japanese Office Action corresponding to JP 2011-160126 dated Jan. 9, 2015.
Japanese Office Action corresponding to JP 2011-184521 dated Jan. 15, 2015.
Extended European Search Report corresponding to 14 18 2236.1 dated Jan. 20, 2015.
Chinese Office Action corresponding to CN 201110201736.1 dated Feb. 9, 2015.
Extended European Search Report corresponding to EP 14 16 1540.1 dated Feb. 27, 2015.
Australian Office Action corresponding to AU 2010226985 dated Mar. 31, 2015.
Australian Office Action corresponding to AU 2013211526 dated Apr. 6, 2015.
Australian Office Action corresponding to AU 2011211463 dated Apr. 13, 2015.
Australian Office Action corresponding to AU 2013254887 dated Apr. 14, 2015.
Japanese Office Action corresponding to JP 2013-225272 dated May 1, 2015.

* cited by examiner

MODULAR SURGICAL CLIP CARTRIDGE

CROSS-REFERENCE TO RELATED APPLICATION

This application claims the benefit of and priority to U.S. Provisional Patent Application No. 62/581,134 filed Nov. 3, 2017, the entire disclosure of which is incorporated by reference herein.

BACKGROUND

1. Technical Field

The present disclosure relates to surgical clip cartridges, and more particularly, to modular surgical clip cartridges.

2. Background of Related Art

Surgical clips are used in a variety of surgical procedures. For example, a surgical clip may be applied to a blood vessel during a procedure to prevent the flow of fluids therethrough. Prior to use, some types of surgical clips are maintained in a clip cartridge to keep the surgical clips secure and/or protected until such time when the surgical clips are needed for a procedure. Typically, the clip cartridge is manufactured and assembled having a set number of surgical clips (e.g., 6 per cartridge) therein. It is often the case that surgical procedures require more, or less, surgical clips than are disposed within a single clip cartridge.

Accordingly, a need exists for a modular clip cartridge that can be assembled to contain a variable amount of surgical clips.

SUMMARY

According to an aspect of the present disclosure, a modular surgical clip pack is provided, including a first modular clip cartridge and a second modular clip cartridge. Each modular clip cartridge includes a body portion having a first wall and a second wall. The first wall defines a first protuberance, a second protuberance symmetrically opposed to the first protuberance, and a first mating feature disposed between the first and second protuberances. The second wall defines a first recess, a second recess symmetrically opposed to the first recess, and a second mating feature disposed between the first and second recesses. At least one clip compartment is defined in the body portion and is configured to releasably retain at least one surgical clip therein.

One of the first mating feature and the second mating feature of the first modular clip cartridge is configured to selectively engage one of the first mating feature and the second mating feature of the second modular clip cartridge to selectively connect the first and second modular clip cartridges into a unitary arrangement to define the modular surgical clip pack.

The first and second protuberances of one of the first and second modular clip cartridges is configured to selectively engage with the first and second recesses of one of the first and second modular clip cartridges to lock the first and second modular clip cartridges into the unitary arrangement.

In embodiments, the first mating feature includes a rail formed on the first wall and the second mating feature includes a slot formed in the second wall. One of the slot or the rail of the first modular clip cartridge is configured to slidably engage one of the slot or the rail of the second modular clip cartridge to selectively connect the first and second modular clip cartridges into the unitary arrangement and define the modular surgical clip pack.

In some embodiments, the rail extends between a top end of the first wall to a bottom end of the first wall, and the slot extends from a top end of the second wall to a bottom end of the second wall.

In certain embodiments, the rail is disposed on a central portion of the first wall, and the slot is disposed on a central portion of the second wall.

In embodiments, the first and second protuberances of one of the first and second modular clip cartridges and the first and second recesses of one of the first and second modular clip cartridges are snap-fit connectable to each other.

In some embodiments, each of the first and second protuberances defines a circular cross-sectional shape.

In certain embodiments, the body portion includes a third wall and a fourth wall. The third and fourth walls are parallel relative to each other and extend between and interconnect the first and second walls to define at least one of a rectangular and a cube shape of each modular surgical clip cartridge.

In embodiments, each wall defines an inner surface and an outer surface. The at least one clip compartment is defined by the inner surface of at least one of the first, second, third, and fourth walls.

In some embodiments, the at least one clip compartment includes a pair of wall dividers that are parallel to the first and second walls and extend between and interconnect the third and fourth walls. The pair of wall dividers define three separate clip compartments in the at least one clip compartment. Each of the three separate clip compartments contain the at least one surgical clip therein.

In certain embodiments, the at least one surgical clip includes at least one of a metallic clip or a polymeric clip.

In embodiments, the at least one clip compartment is configured to receive a surgical instrument for removing the at least one surgical clip therefrom.

In some embodiments, the surgical instrument is selected from the group consisting of forceps, graspers, and a surgical clip applier.

According to another aspect of the present disclosure, a modular clip cartridge is provided, including a body portion having a first wall and a second wall. The first wall defines a first protuberance, a second protuberance symmetrically opposed to the first protuberance, and a first mating feature disposed between the first and second protuberances. The second wall defines a first recess, a second recess symmetrically opposed to the first recess, and a second mating feature disposed between the first and second recesses. At least one clip compartment is defined in the body portion and configured to releasably retain at least one surgical clip therein.

One of the first mating feature and the second mating feature of the modular clip cartridge is configured to selectively engage one of a first mating feature and a second mating feature of another modular clip cartridge to selectively connect the first modular clip cartridge and another modular clip cartridge into a unitary arrangement to define a modular surgical clip pack.

In embodiments, the first and second protuberances of the modular clip cartridge are configured to selectively engage with first and second recesses of another modular clip cartridge. The first and second recesses of the modular clip cartridge are configured to selectively receive first and second protuberances of another modular clip cartridge to lock the modular clip cartridge into a unitary arrangement with at least one other modular clip cartridge.

In some embodiments, the body portion includes a third wall and a fourth wall that are parallel relative to each other. The third and fourth walls extend between and interconnect the first and second walls to define at least one of a rectangular and a cube shape of the modular surgical clip cartridge.

In certain embodiments, each wall defines an inner surface and an outer surface. The at least one clip compartment is defined by the inner surface of at least one of the first, second, third, and fourth walls.

In embodiments, the at least one clip compartment includes a pair of wall dividers that are parallel to the first and second walls and extend between and interconnect the third and fourth walls. The pair of wall dividers define three separate clip compartments in the at least one clip compartment. Each of the three separate clip compartments contain the at least one surgical clip therein.

In some embodiments, each of the first and second protuberances defines a circular cross-sectional shape.

In certain embodiments, the first mating feature includes a rail formed on the first wall and the second mating feature includes a slot formed in the second wall.

In embodiments, the rail is disposed on a central portion of the first wall between the first and second protuberances, and the slot is disposed on a central portion of the second wall between the first and second recesses.

BRIEF DESCRIPTION OF THE DRAWINGS

Objects and features of the present disclosure will become apparent to those of ordinary skill in the art when descriptions thereof are read with reference to the accompanying drawings, of which.

DETAILED DESCRIPTION

Figure 1B:
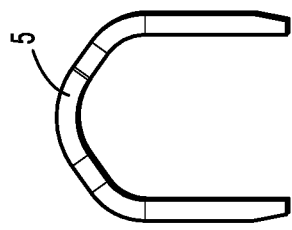
FIG. 1B is a perspective view of a surgical clip for use with the modular surgical clip cartridge of FIG. 1A.

Embodiments of modular surgical clip cartridges, in accordance with the present disclosure, will now be described in detail with reference to the drawing figures wherein like reference numerals identify similar or identical structural elements. Aspects and features of the modular surgical clip cartridges depicted herein, not germane to the understanding of the present disclosure, are omitted to avoid obscuring the aspects and features of the present disclosure in unnecessary detail.

The present disclosure is directed to modular surgical clip cartridges configured to create clip packs retaining surgical clips of varying quantities. Specifically, the modular clip cartridges described herein are configured to selectively connect with one another, into a unitary arrangement, to define a modular clip pack. Any number of modular surgical clip cartridges can be connected with one another to form modular clip packs to define a variable number of surgical clip quantities. The modular clip cartridges can be, e.g., shipped and packed individually, and then assembled into modular clip packs as needed, enabling end users greater flexibility in planning surgical procedures, while reducing the overall costs of manufacture thereof.

Figure 1A:
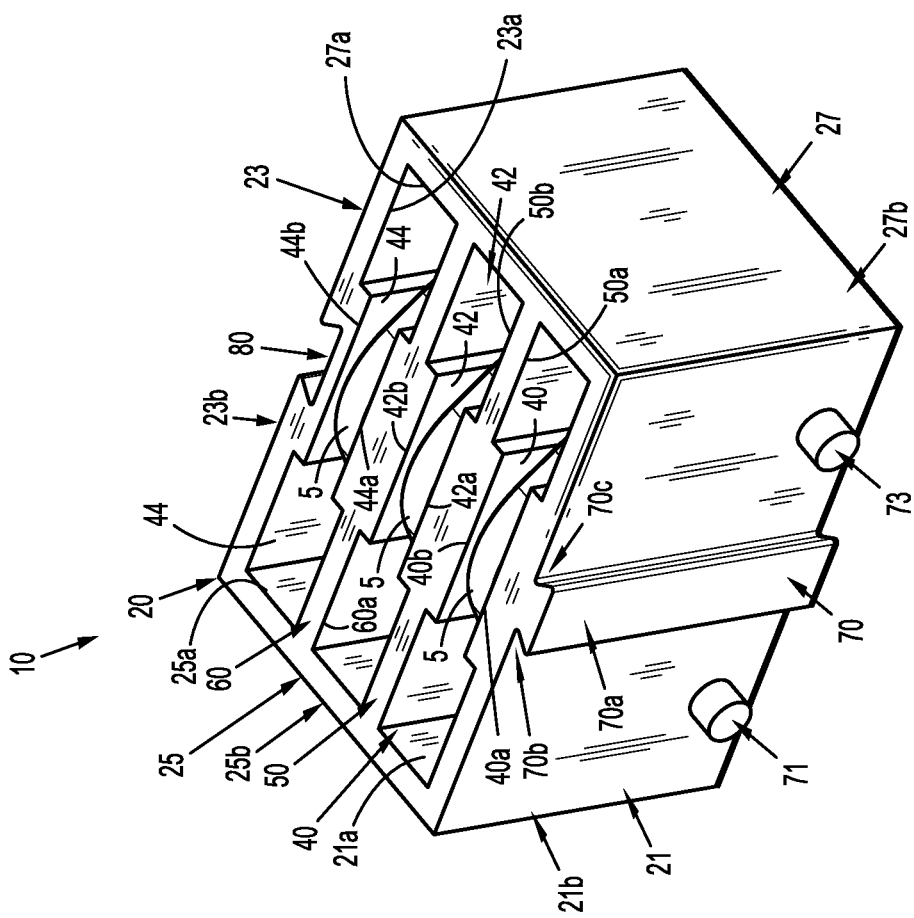
FIG. 1A is a perspective view of a modular surgical clip cartridge in accordance with the present disclosure.
Figure 2:
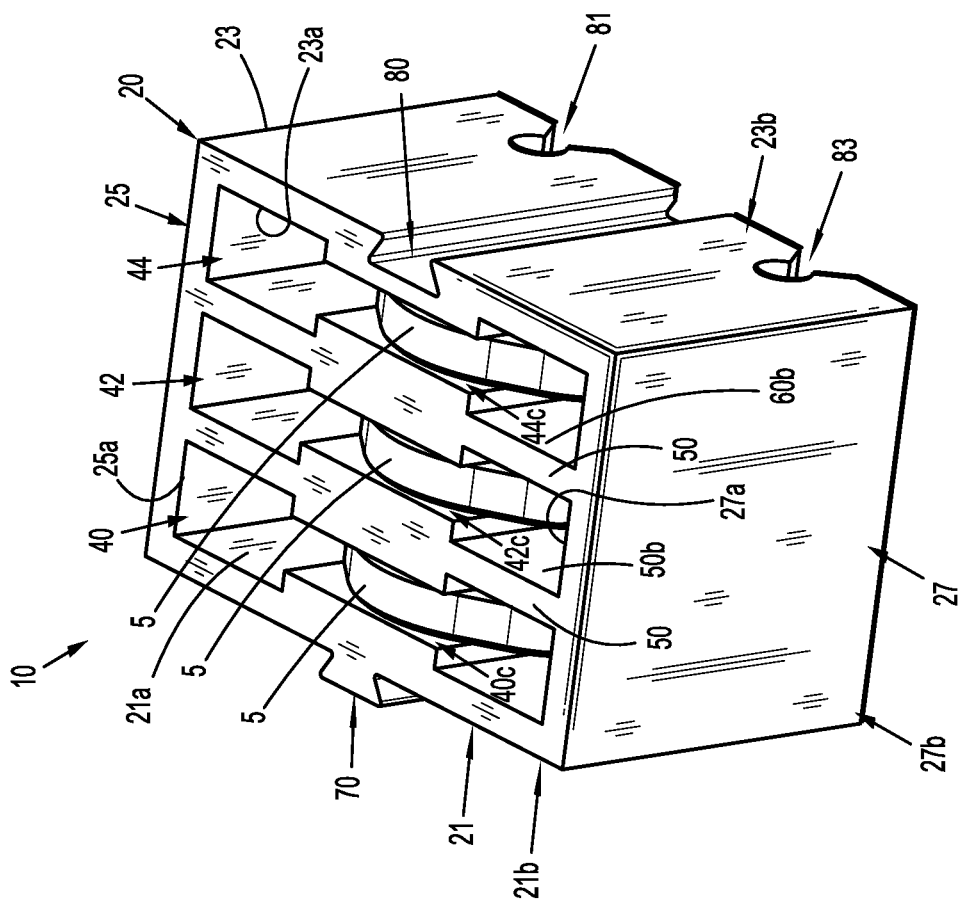
FIG. 2 is another perspective view of the modular surgical clip cartridge of FIG. 1A.

Referring initially to FIGS. 1A, 1B, and 2, a modular clip cartridge in accordance with the present disclosure is shown and generally designated as 10. Modular clip cartridge 10 includes a body portion 20 generally defining respective first, second, third, and fourth walls 21, 23, 25, 27 and a plurality of clip compartments 40, 42, 44. Each clip compartment 40, 42, 44 is configured to releasably retain a surgical clip 5 therein.

First and second walls 21, 23 of body portion 20 (e.g., top and bottom walls) are parallel relative to each other. Likewise, third and fourth walls 25, 27 of body portion 20 (e.g., sidewalls) are parallel and spaced apart relative to each other, and extend between and interconnect first and second walls 21, 23. First wall 21 defines respective inner and outer surfaces 21a, 21b, second wall 23 defines respective inner and outer surfaces 23a, 23b, third wall 25 defines respective inner and outer surfaces 25a, 25b, and fourth wall 27 defines respective inner and outer surfaces 27a, 27b. Respective first, second, third, and fourth walls 21, 23, 25, 27 of body portion 20 collectively define a rectangular or cube shape of modular clip cartridge 10, although any other suitable shape or configuration (e.g., circular, trapezoidal, triangular, etc.) of modular clip cartridge 10 is contemplated.

Body portion 20 defines a first wall divider 50 and a second wall divider 60, extending between and interconnecting third and fourth walls 25, 27 to define individual clip compartments 40, 42, 44. First wall divider 50 defines respective lower and upper surfaces 50a, 50b. Likewise, second wall divider 60 defines respective lower and upper surfaces 60a, 60b. First and second wall dividers 50, 60 may be oriented parallel to first and second walls 21, 23 of body portion 20. Although modular clip cartridge 10 is shown as having two wall dividers 50, 60 to define three individual clip compartments 40, 42, 44 within body portion 20, it is contemplated that modular clip cartridge 10 may have any number of clip compartments (e.g., one, two, four, five, six, seven, etc.) for retaining any number of surgical clips 5 therein.

Clip compartment 40 defines a ledge or side edge 40a extending from inner surface 21a of first wall 21, and defines a ledge or side edge 40b extending from upper surface 50a of first wall divider 50 towards side edge 40a. Ledges or side edges 40a, 40b of clip compartment 40 define a reduced width, central portion 40c of clip compartment 40. Likewise, clip compartment 42 defines a ledge or side edge 42a extending from lower surface 50b of first wall divider 50, and defines a ledge or side edge 42b extending from lower surface 60a of second wall divider 60 toward side edge 42a. Ledges or side edges 42a, 42b define a reduced width, central portion 42c of clip compartment 42. In addition, clip compartment 44 defines a ledge or side edge 44a extending from lower surface 60b of first wall divider 60, and defines a ledge or side edge 44b extending from inner surface 23a second wall 23 toward side edge 44a. Ledges or side edges 44a, 44b define a reduced width, central portion 44c of clip compartment 44. As such, reduced width, central portions 40c, 42c, 44c of respective clip compartments 40, 42, 44 define clip compartments 40, 42, 44 having a substantially dog-bone shaped transverse cross-section profile. In embodiments, reduced width, central portions 40c, 42c, 44c may frictionally engage with surgical clips 5 to releasably retain surgical clips 5 therein.

Outer surface 21b of first wall 21 defines a first mating feature or rail 70 extending therefrom. Rail 70 extends from a top end of outer surface 21b of first wall 21 to a bottom end of outer surface 21b of first wall 21. Rail 70 may be located along a central portion or center line of outer surface 21b of first wall 21. Rail 70 is defined by a flat face 70a, and two inwardly extending side edges or undercuts 70b, 70c that terminate into outer surface 21b of first wall 21 (e.g., in the form of a dove tail). Although rail 70 is shown as having a trapezoidal, transverse cross-sectional shape, rail 70 can be configured with any suitable shape, size, or configuration (e.g., rectangular, triangular, semi-circular, etc.).

Outer surface 21b of first wall 21 further defines first and second protuberances or bosses 71, 73 extending therefrom. First protuberance 71 may be disposed on a first side of rail 70, while second protuberance 73 may be disposed on a second side of rail 70. Protuberances 71, 73 may be disposed on a lower end portion of outer surface 21b of first wall 21 (e.g., adjacent an end or edge thereof) and may be symmetrically opposed to each other. Protuberances 71, 73 are shown as having a circular, transverse cross-sectional shape, but any suitable shape is contemplated, such as, e.g., triangular, spherical, rectangular, trapezoidal, or the like. Modular clip cartridge 10 may include one, or more than the two protuberances 71, 73 shown in FIG. 1A.

Outer surface 23b of second wall 23 defines a second mating feature or slot 80 therein having a shape complementary to that of rail 70. Slot 80 is configured to slidably receive a rail 70' of a second modular clip cartridge 10' to selectively connect first modular clip cartridge 10 to another, e.g., second modular clip cartridge 10' to define a modular clip pack 100 (FIGS. 3A and 3B), as will be more fully described below. Slot 80 may extend from a top end or edge of outer surface 23b of second wall 23 to a bottom end of outer surface 23b of second wall 23.

Second wall 23 further defines first and second recesses 81, 83 therein having a shape complementary to that of first and second protuberances 71, 73 of first wall 21. Recesses 81, 83 are configured to frictionally engage with protuberances 71', 73' (not explicitly shown) of second modular clip cartridge 10' (FIGS. 3A and 3B) to at least temporally lock first modular clip cartridge 10 to another, e.g., second modular clip cartridge 10', as will be more fully described below. First recess 81 may be formed into a first side of second wall 23, while second recess 83 may be formed into a second side of second wall 23. Recesses 81, 83 may be defined through a bottom end portion of second wall 23. First and second recesses 81, 83 may be symmetrically opposed to each other. Recesses 81, 83 are shown as having a substantially keyhole like shape or configuration, but any suitable shape of recesses 81, 83 is contemplated.

Figure 3B:
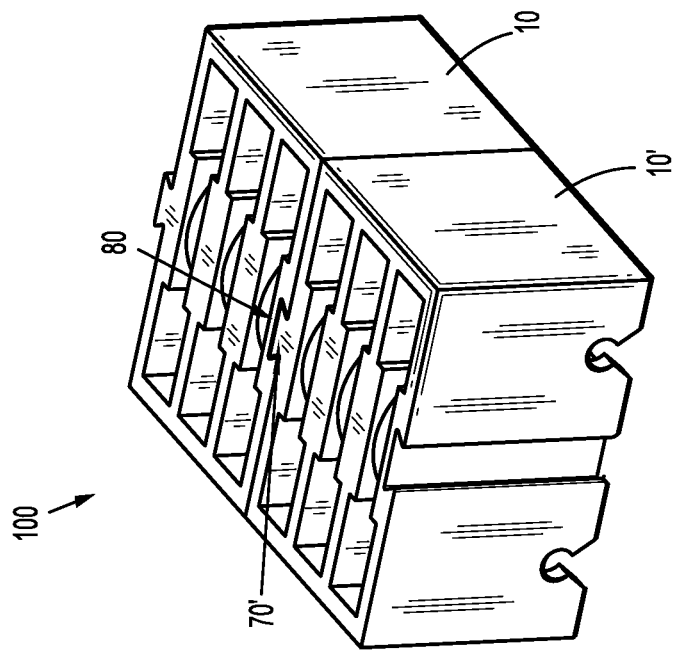
FIG. 3B is another perspective view of the modular clip pack of FIG. 3A.
Figure 3A:
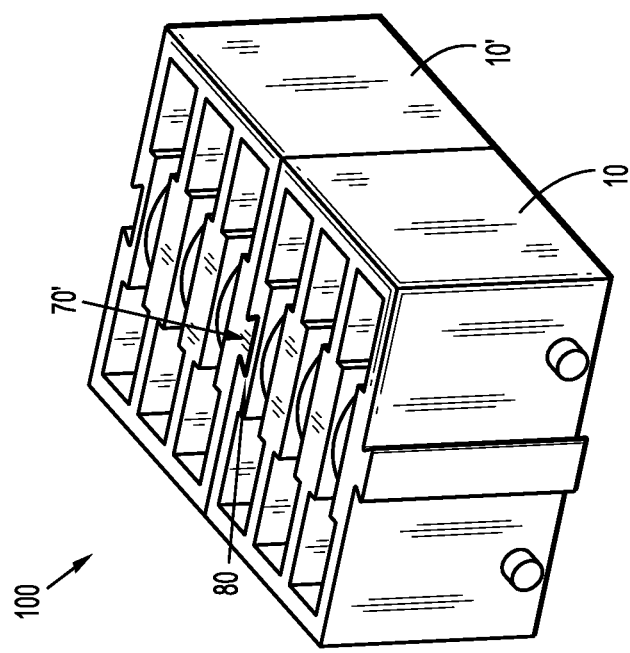
FIG. 3A is a perspective view of two modular surgical clip cartridges selectively connected to one another define a modular clip pack.

In use, with reference to FIGS. 3A and 3B, slot 80 of first modular clip cartridge 10 slidably engages rail 70' of a second modular clip cartridge 10' to selectively connect first and second modular clip cartridges 10, 10' into a unitary arrangement and define a modular surgical clip pack 100. Specifically, with slot 80 of first modular clip cartridge 10 and rail 70' of second modular clip cartridge at least initially slidably engaged with each other, continued movement of slot 80 and rail 70' of respective first and second modular clip cartridges 10, 10' along each other causes first and second modular clip cartridges 10, 10' to fully join together into a unitary arrangement. As such, slot 80 and rail 70' of first and second modular clip cartridges 10, 10' function as a "tongue-and-groove" arrangement to form modular surgical clip pack 100.

In addition, in use, continued movement of slot 80 and rail 70' of respective first and second modular clip cartridges 10, 10' towards each other causes recesses 81, 83 of first modular clip cartridge 10 and protuberances 71, 73 of second modular clip cartridge 10' to frictionally engage with each other (not explicitly shown), causing first modular clip cartridge 10 and second modular clip cartridge 10' to at least temporarily lock into a unitary arrangement, e.g., into modular surgical clip pack 100. In embodiments, recesses 81, 83 of first modular clip cartridge 10 may have any type of connection with protuberances 71', 73' of second modular clip cartridge 10', such as for example, snap-fit, compression-fit, frictional-fit, or the like.

To disassemble modular clip pack 100, modular clip cartridge 10 is moved (e.g., slid) relative to second modular clip cartridge 10' such that recesses 81, 83 of modular clip cartridge 10 disengage from respective protuberances 71, 73 of second modular clip cartridge 10'. As such, modular clip pack 100 can be assembled and disassembled as needed.

Thus, advantageously, first and second modular clip cartridges 10, 10' can be, e.g., shipped and packed individually, and then assembled (or disassembled) into modular clip packs 100 as needed, enabling end users greater flexibility in planning surgical procedures, while reducing the overall cost of manufacture thereof.

Although two clip cartridges are shown as connected in FIGS. 3A and 3B of the present disclosure, it should be appreciated that any number of clip cartridges 10 may be connected with each other to define modular clip pack 100. In embodiments, rail 70, slot 80, protuberances 71, 73, and recesses 81, 83 may be formed onto and/or into any and/or all surfaces of modular clip cartridge 10 (e.g., third wall 25, fourth wall 27, etc.), such that modular clip cartridge 10 can be adjoined with other modular clip cartridges at additional points of connectivity, enabling end users with more flexibility. Additionally, although rail 70 is shown as being on the same surface as protuberances 71, 73, and slot 80 is shown as being on the same surface as recesses 81, 83, it should be appreciated that rail 70 may be formed on the same surface as recesses 81, 83, slot 80 may be formed on same surface as protuberances 71, 73, etc.

In embodiments, modular clip cartridge 10 may be formed from any suitable material, such as from plastics, polymers, ceramics, metals, and/or the like. Clip compartments 40 may be configured to receive any type of surgical clip 5 with any type of geometry, such as, for example, the surgical clips described in commonly assigned U.S. Pat. No. 5,501,693 to Gravener, the entire contents of which is hereby incorporated by reference. Surgical clips 5 may include at least one of a metallic or polymeric material. In embodiments, clip compartments 40 of modular clip cartridge 10 may be configured to receive jaws of a surgical instrument for removing surgical clips therefrom. Such surgical instruments may include, but are not limited to, forceps, graspers, surgical clip appliers, etc.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A modular surgical clip pack, comprising:
a first modular clip cartridge and a second modular clip cartridge, each modular clip cartridge including:
a body portion including:
a first wall defining a first protuberance, a second protuberance symmetrically opposed to the first protuberance, and a first mating feature disposed between the first and second protuberances; and
a second wall defining a first recess, a second recess symmetrically opposed to the first recess, and a second mating feature disposed between the first and second recesses;
at least one clip compartment defined in the body portion configured to releasably retain at least one surgical clip therein; and
wherein one of the first mating feature and the second mating feature of the first modular clip cartridge is configured to selectively engage one of the first mating feature and the second mating feature of the second modular clip cartridge to selectively connect the first and second modular clip cartridges into a unitary arrangement to define the modular surgical clip pack,
wherein the first and second protuberances of one of the first and second modular clip cartridges is configured to selectively engage with the first and second recesses of one of the first and second modular clip cartridges to lock the first and second modular clip cartridges into the unitary arrangement,
wherein at least one of the first recess or the second recess extends through the second wall and a third wall of the body portion.

2. The modular surgical clip pack of claim 1, wherein the first mating feature includes a rail formed on the first wall and the second mating feature includes a slot formed in the second wall, wherein one of the slot or the rail of the first modular clip cartridge is configured to slidably engage one of the slot or the rail of the second modular clip cartridge to selectively connect the first and second modular clip cartridges into the unitary arrangement and define the modular surgical clip pack.

3. The modular surgical clip pack of claim 2, wherein the rail extends between a top end of the first wall to a bottom end of the first wall, and wherein the slot extends from a top end of the second wall to a bottom end of the second wall.

4. The modular surgical clip pack of claim 3, wherein the rail is disposed on a central portion of the first wall, and the slot is disposed on a central portion of the second wall.

5. The modular surgical clip pack of claim 1, wherein the first and second protuberances of one of the first and second modular clip cartridges and the first and second recesses of one of the first and second modular clip cartridges are snap-fit connectable to each other.

6. The modular surgical clip pack of claim 1, wherein each of the first and second protuberances defines a circular cross-sectional shape.

7. The modular surgical clip pack of claim 1, wherein the body portion includes a fourth wall, the third and fourth walls being parallel relative to each other, the third and fourth walls extending between and interconnecting the first and second walls to define at least one of a rectangular and a cube shape of each modular surgical clip cartridge.

8. The modular surgical clip pack of claim 7, wherein each wall defines an inner surface and an outer surface, and wherein the at least one clip compartment is defined by the inner surface of at least one of the first, second, third, and fourth walls.

9. The modular surgical clip pack of claim 8, wherein the at least one clip compartment includes a pair of wall dividers that are parallel to the first and second walls and extend between and interconnect the third and fourth walls, the pair of wall dividers defining three separate clip compartments in the at least one clip compartment, each of the three separate clip compartments configured to contain at least one surgical clip therein.

10. The modular surgical clip pack of claim 1, wherein the at least one surgical clip includes at least one of a metallic clip or a polymeric clip.

11. The modular surgical clip pack of claim 1, wherein the at least one clip compartment is configured to receive a surgical instrument for removing the at least one surgical clip therefrom.

12. The modular surgical clip pack of claim 11, wherein the surgical instrument is selected from the group consisting of forceps, graspers, and a surgical clip applier.

13. A modular clip cartridge, comprising:
a body portion including:
a first wall defining a first protuberance, a second protuberance symmetrically opposed to the first protuberance, and a first mating feature disposed between the first and second protuberances;
a second wall defining a first recess, a second recess symmetrically opposed to the first recess, and a second mating feature disposed between the first and second recesses; and
at least one clip compartment defined in the body portion, the at least one clip compartment configured to releasably retain at least one surgical clip therein;
wherein one of the first mating feature and the second mating feature of the modular clip cartridge is configured to selectively engage one of a first mating feature and a second mating feature of another modular clip cartridge to selectively connect the first modular clip cartridge and another modular clip cartridge into a unitary arrangement to define a modular surgical clip pack,
wherein at least one of the first recess or the second recess extends through the second wall and a third wall of the body portion.

14. The modular clip cartridge of claim 13, wherein the first and second protuberances of the modular clip cartridge are configured to selectively engage with first and second recesses of another modular clip cartridge, and wherein the first and second recesses of the modular clip cartridge are configured to selectively receive first and second protuberances of another modular clip cartridge to lock the modular clip cartridge into a unitary arrangement with at least one other modular clip cartridge.

15. The modular clip cartridge of claim 13, wherein the body portion includes a third wall and a fourth wall, the third and fourth walls being parallel relative to each other, the third and fourth walls extending between and interconnecting the first and second walls to define at least one of a rectangular and a cube shape of the modular surgical clip cartridge.

16. The modular clip cartridge of claim 15, wherein each wall defines an inner surface and an outer surface, and wherein the at least one clip compartment is defined by the inner surface of at least one of the first, second, third, and fourth walls.

17. The modular clip cartridge of claim 16, wherein the at least one clip compartment includes a pair of wall dividers that are parallel to the first and second walls and extend between and interconnect the third and fourth walls, the pair of wall dividers defining three separate clip compartments in the at least one clip compartment, each of the three separate clip compartments containing the at least one surgical clip therein.

18. The modular clip cartridge of claim 13, wherein each of the first and second protuberances defines a circular cross-sectional shape.

19. The modular clip cartridge of claim 13, wherein the first mating feature includes a rail formed on the first wall and the second mating feature includes a slot formed in the second wall.

20. The modular clip cartridge of claim 19, wherein the rail is disposed on a central portion of the first wall between the first and second protuberances, and the slot is disposed on a central portion of the second wall between the first and second recesses.

21. The modular surgical clip pack of claim 1, wherein the second wall and the third wall of the body portion are perpendicular to each other.

22. The modular surgical clip pack of claim 1, wherein the first and second protuberances of the first modular clip cartridge are configured to simultaneously engage the first and second recesses of the second modular clip cartridge, respectively, in a single, linear direction to lock the first and second modular clip cartridges into the unitary arrangement.

\* \* \* \* \*